(12) United States Patent
    Sardari et al.

(10) Patent No.: US 11,696,997 B2
(45) Date of Patent: *Jul. 11, 2023

(54) MEDICAL DEVICE FLUSHING SYSTEMS AND METHODS

(71) Applicant: KARDIUM INC., Burnaby (CA)

(72) Inventors: Ashkan Sardari, North Vancouver (CA); Saar Moisa, Vancouver (CA); John Andrew Funk, Delta (CA)

(73) Assignee: KARDIUM INC., Burnaby (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/485,880

(22) Filed: Sep. 27, 2021

(65) Prior Publication Data

US 2022/0008690 A1    Jan. 13, 2022

Related U.S. Application Data

(63) Continuation of application No. 15/986,188, filed on May 22, 2018, now Pat. No. 11,160,950, which is a
(Continued)

(51) Int. Cl.
    *A61M 25/00* (2006.01)
    *A61M 5/36* (2006.01)
    (Continued)

(52) U.S. Cl.
    CPC .............. *A61M 25/00* (2013.01); *A61M 5/36* (2013.01); *A61B 5/287* (2021.01); *A61B 5/6858* (2013.01);
    (Continued)

(58) Field of Classification Search
    CPC ................ A61B 18/00; A61B 18/1492; A61B 2018/00214; A61B 2018/00267;
    (Continued)

(56) References Cited

U.S. PATENT DOCUMENTS 4,127,141 A    11/1978 Ledonne
4,306,705 A    12/1981 Svensson
    (Continued)

FOREIGN PATENT DOCUMENTS

CA    2877699 A1    2/2014
FR    2284303 A1    4/1976
    (Continued)

OTHER PUBLICATIONS

Amendment filed in copending U.S. Appl. No. 16/777,248 on Oct. 19, 2021.

(Continued)

*Primary Examiner* — Shefali D Patel
(74) *Attorney, Agent, or Firm* — Rossi, Kimms & McDowell LLP

(57) ABSTRACT

A distal end portion of an elongate shaft member of a catheter may be inserted into a liquid within a vessel. While the distal end portion of the elongate shaft member is inserted in the liquid in the vessel, a manipulable portion of the catheter may be manipulated within the liquid to remove an undesired fluid therefrom. The liquid may be pressurized to cause the liquid to flow into a lumen of the elongate shaft member from a distal end of the elongate shaft member at least toward a proximal end of the elongate shaft member to facilitate flushing of the undesired fluid from the lumen. The distal end portion of the elongate shaft member of the catheter may be inserted into the liquid within the vessel while at least the elongate shaft member is in a substantially horizontal orientation.

31 Claims, 20 Drawing Sheets

Related U.S. Application Data continuation of application No. PCT/CA2016/000298, filed on Dec. 1, 2016.

(60) Provisional application No. 62/281,283, filed on Jan. 21, 2016.

(51) Int. Cl.

| | |
|---|---|
| A61M 39/22 | (2006.01) |
| A61B 5/00 | (2006.01) |
| A61B 18/14 | (2006.01) |
| A61B 5/287 | (2021.01) |
| A61B 18/00 | (2006.01) |
| A61M 5/14 | (2006.01) |

(52) U.S. Cl.
CPC ............ *A61B 5/7264* (2013.01); *A61B 18/00* (2013.01); *A61B 18/1492* (2013.01); *A61B 2018/00267* (2013.01); *A61B 2018/00577* (2013.01); *A61B 2018/00839* (2013.01); *A61B 2218/002* (2013.01); *A61M 39/22* (2013.01); *A61M 2005/1403* (2013.01); *A61M 2025/0019* (2013.01); *A61M 2209/10* (2013.01)

(58) Field of Classification Search
CPC .......... A61B 2018/00577; A61B 2018/00839; A61B 2218/002; A61B 5/6855; A61B 5/6856; A61B 5/6857; A61B 5/6858; A61M 2005/1403; A61M 2025/0019; A61M 2209/10; A61M 25/00; A61M 25/0074; A61M 25/0082; A61M 39/22; A61M 5/36

See application file for complete search history.

(56) References Cited

U.S. PATENT DOCUMENTS

| | | | |
|---|---|---|---|
| 4,576,199 | A | 3/1986 | Svensson |
| 4,745,907 | A | 5/1988 | Russel, Jr. et al. |
| 4,968,309 | A | 11/1990 | Andersson |
| 5,454,792 | A | 10/1995 | Tennican et al. |
| 5,755,894 | A | 5/1998 | Bowman |
| 5,951,581 | A | 9/1999 | Saadat |
| 6,514,261 | B1 | 2/2003 | Randall et al. |
| 6,641,564 | B1 | 11/2003 | Kraus |
| 6,932,795 | B2 | 8/2005 | Lopez |
| 7,137,974 | B2 | 11/2006 | Almasian |
| 7,708,714 | B2 | 5/2010 | Connell |
| 7,828,269 | B2 | 11/2010 | Iversen |
| 9,033,953 | B2 | 5/2015 | Felber |
| 9,452,016 | B2 | 9/2016 | Moisa et al. |
| 9,528,649 | B2 | 12/2016 | Aoki |
| 2002/0007152 | A1 | 1/2002 | Hermann |
| 2003/0032922 | A1 | 2/2003 | Moorehead |
| 2005/0096647 | A1 | 5/2005 | Steinke |
| 2008/0200791 | A1 | 8/2008 | Simpson |
| 2009/0270815 | A1 | 10/2009 | Stamp |
| 2013/0345673 | A1 | 12/2013 | Ferreri et al. |
| 2014/0236275 | A1 | 8/2014 | Thompson et al. |
| 2016/0166821 | A1 | 6/2016 | Weiss |
| 2016/0220741 | A1 | 8/2016 | Garrison et al. |
| 2018/0264230 | A1 | 9/2018 | Funk et al. |
| 2018/0296233 | A1 | 10/2018 | Schwager |
| 2019/0358430 | A1 | 11/2019 | Sardari |

FOREIGN PATENT DOCUMENTS

| | | |
|---|---|---|
| WO | 9908931 A1 | 2/1999 |
| WO | 2007109257 A2 | 9/2007 |
| WO | 2015089649 A1 | 6/2015 |
| WO | 2017070801 A1 | 5/2017 |
| WO | 2017100902 A1 | 6/2017 |
| WO | 2019213742 A1 | 11/2019 |

OTHER PUBLICATIONS

Notice of Allowance issued in copending U.S. Appl. No. 16/777,248 dated Dec. 10, 2021.
Copending U.S. Appl. No. 17/564,388, filed Dec. 29, 2021.
Extended European Search Report issued in European Application No. 19799136.7 dated Jan. 12, 2022.
Non-Final Office Action issued in copending U.S. Appl. No. 16/777,248 dated Jul. 27, 2021.
Notice of Allowance issued in copending U.S. Appl. No. 17/564,388 dated May 3, 2022.
International Search Report issued in Intl. Appln. No. PCT/CA2019/050381 dated Jun. 5, 2019.
Written Opinion issued in Intl. Appln. No. PCT/CA2019/050381 dated Jun. 5, 2019.
International Search Report issued in Intl. Appln. No. PCT/CA2016/000298 dated Feb. 20, 2017.
Written Opinion issued in Intl. Appln. No. PCT/CA2016/000298 dated Feb. 20, 2017.
Mounsey. "A novel multielectrode combined mapping and ablation basket catheter: A future player in the atrial fibrillation ablation space?" Journal of Cardiovascular Electrophysiology. 2017:1-2.
Kottkamp et al. "Global multielectrode contact mapping plus ablation with a single catheter: Preclinical and preliminary experience in humans with atrial fibrillation." Journal of Cardiovascular Electrophysiology. 2017:1-10.
Notice of Allowance received in U.S. Appl. No. 16/535,471 dated Nov. 27, 2019.
Office Action issued in copending U.S. Appl. No. 15/986,188 dated Jan. 28, 2021.
Amendment filed in copending U.S. Appl. No. 15/986,188 dated Apr. 22, 2021.
Notice of Allowance issued in copending U.S. Appl. No. 15/986,188 dated Aug. 11, 2021.

900A

PROVIDE, VIA A SECOND PORT OF THE VESSEL, A QUANTITY OF PARTICULAR FLUID OTHER THAN THE LIQUID INTO SECOND PORTION OF INTERIOR CAVITY WHILE AT LEAST SOME OF THE LIQUID IS IN THE FIRST PORTION OF THE INTERIOR CAVITY — 920

*FIG. 8D*

MEDICAL DEVICE FLUSHING SYSTEMS AND METHODS

CROSS-REFERENCE TO RELATED APPLICATIONS

This application is a continuation of U.S. application Ser. No. 15/986,188, filed May 22, 2018, now U.S. Pat. No. 11,160,950, issued Nov. 2, 2021, which is a continuation of International Application No. PCT/CA2016/000298, filed on Dec. 1, 2016, which claims the benefit of U.S. Provisional Application No. 62/281,283, filed Jan. 21, 2016, the entire disclosure of each of these applications is hereby incorporated herein by reference.

TECHNICAL FIELD

Aspects of this disclosure generally are related to apparatus and methods for flushing a medical system, such as a catheter system, of an undesired fluid. In some embodiments, the catheter system includes a controllable manipulable portion.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During various procedures, health care providers create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy, and cryogenic techniques. The procedure is performed with a high success rate under the direct vision that is provided in open procedures, but is relatively complex to perform intravascularly or percutaneously because of the difficulty in creating the lesions in the correct locations.

Preparation of catheter device systems for subsequent delivery through a bodily opening leading to a bodily cavity (e.g., as required by some percutaneous or intravascular procedures) may require that various fluids (e.g., air) be purged or otherwise removed from portions of the systems prior to insertion into the body. Failure to do so may allow for a transfer of at least some of the fluids to within the body which may in turn result in various undesired outcomes (e.g., the formation of various air embolisms). Various catheter device systems employ various features that can act as fluid traps from which undesired fluid can be difficult to remove therefrom. For example, various lumens comprised by various catheter device systems may act as fluid traps. FIG. 7A is a schematic that shows at least part of a conventional catheter system that includes a catheter sheath 812 including a lumen that provides a passageway for a catheter member (not shown) delivered through a bodily opening during a medical procedure. A dilator 800 is typically inserted through the lumen of the catheter sheath 812 from the proximal end 812*a* of the catheter sheath 812 to the distal end 812*b* of the catheter sheath 812. A point-like end 813 of the dilator 800 typically protrudes from the distal end 812*b* of the catheter shaft 812 when the dilator 800 is operably inserted into the lumen of the catheter sheath 812. The dilator 800/catheter sheath 812 assembly are then advanced through the bodily opening with the protruding point-like end 813 of the dilator 800 dilating or enlarging various parts of the bodily opening to facilitate the advancement of the assembly through the bodily opening. Once the assembly has been successfully delivered through the bodily opening to a desired location within the body, the dilator 800 is pulled out of the catheter sheath 812 leaving the catheter sheath 812 behind in the bodily opening. A catheter or other medical instrument is then advanced through the lumen of the catheter sheath 812 to the desired location within the body.

It is noted that undesired fluid (e.g., air) may be present, for example, in the lumen of the catheter sheath 812, at least before or after the insertion of the dilator 800 into the lumen. This undesired fluid requires removal (e.g., to avoid introducing the undesired fluid in the body) prior to advancement of the assembly of the dilator 800/catheter sheath 812 through the bodily opening. Conventional catheter systems attempt to flush the undesired fluid by introducing a liquid, such as saline, into the region of the lumen of the catheter sheath 812 to flush the lumen of the undesired fluid. The introduction of liquid into the lumen of the catheter sheath 812 to remove the undesired fluid therefrom may occur at least before the insertion of the dilator 800 into the lumen or after the insertion of the dilator 800 into the lumen. It is noted that even if the lumen of the catheter sheath 812 is filled with the liquid, the introduction of the dilator into the lumen may introduce undesired fluid into the lumen of the catheter sheath 812 prior to advancement of the assembly though the bodily opening, thereby further complicating the flushing procedure.

FIG. 7B shows a typical flushing procedure employed by conventional catheter systems. A source 802 of liquid 804 (e.g., saline) is fluidly connected to the catheter sheath 812 at a location at least proximate the proximal end 812*a* to attempt to flush a region of the lumen between the dilator 800 and the catheter sheath 812. It is noted that conventional flushing systems flush proximally (near proximal end 812*a*) toward distally (toward distal end 812*b*) because the supply connector 812*c* for the flushing liquid is provided proximally and not distally on the catheter member. In conventional flushing systems, a distal supply connector (e.g., a distal connector located proximate the distal end 812*b* of catheter sheath 812 rather than proximate proximal end 812*a*) would interfere with the introduction of the catheter member into the bodily opening and is therefore not employed.

It is noted that the fit between the dilator 800 and catheter sheath 812 is typically relatively snug and this fit can act as a fluid restriction that may entrap the undesired fluid (e.g., air) when the dilator 800 is advanced into the lumen of the catheter sheath 812. Typically, the assembly of the catheter sheath 812 and dilator 800 is held inclined or vertically (i.e., distal end 812b up) to try to promote conveying any bubbles of the undesired fluid (i.e., which is typically less dense than the liquid) upwards. This orientation may become cumbersome especially when it is required to perform this procedure in a sterile field. Further, it is noted that the flow rate of the flushing liquid 804 is reduced by the supply connector 812c and the supply line 803 coupling the supply connector 812c to the source 802 of liquid 804 (e.g., the supply lumens in the supply connector 812c and the supply line 803 typically have smaller cross-sectional areas (i.e., typically driven by the standardized sizes of various components such as Luer Lock connectors) than the cross-sectional area of the lumen of the catheter sheath 812 into which the dilator 800 is advanced). Reduced flow rates for the flushing liquid 804 may be insufficient to completely flush bubbles of undesired fluid from the lumen of the catheter sheath 812. This condition may be especially prevalent when lumens having relative large cross-sectional areas (e.g., in comparison to the cross-sectional areas of the supply lumens in the supply connector 812c and the supply line 803 coupling the supply connector 812c to the source of liquid 804) thereby increasing the amount of surface area to which the bubbles of the undesired fluid may cling. In some cases, relatively low flow rates of the flushing liquid 804 may merely push many of the clinging smaller bubbles of the undesired fluid together to form larger bubbles of the undesired fluid, which, if subsequently released into the patient, may lead to the formation of even potentially more harmful emboli (i.e., than emboli formed by the smaller bubbles) in some procedures.

Even various materials that may be employed by various catheter device systems may make it difficult to remove undesired fluid. For example, polytetrafluoroethylene (PTFE) is typically employed by various catheter device systems because of its relatively low friction characteristics. However, polytetrafluoroethylene is an example of a material that essentially is hydrophobic in nature, and, thus, can restrict removal of fluid bubbles on a surface thereof when a water-based liquid (e.g., saline) is employed to flush or otherwise remove the fluid bubbles. That is, the flow of the flushing liquid may be insufficient to flush bubbles accumulated on a surface of the lumen, especially when that surface has hydrophobic characteristics which tend to repel the liquid, thereby reducing the flushing ability of the liquid.

It is noted that a catheter member or medical instrument that is subsequently advanced into the lumen of the catheter sheath 812 may also include various internal lumens that require flushing of undesired fluids. Additionally or alternatively, various channels produced by various elements of the catheter member or medical instrument (e.g., converging elongated elements of basket-type catheter devices) may act as fluid traps.

Accordingly, a need in the art exists for systems and methods having improved capabilities for the removal of undesired fluid from medical device systems, such as catheter device systems.

SUMMARY

At least the above-discussed need is addressed and technical solutions are achieved by various embodiments of the present invention. In some embodiments, a flushing kit for flushing a catheter is provided. The catheter includes an elongate shaft member that includes a proximal end, a distal end, a length from the proximal end to the distal end, and at least a first lumen extending between the proximal end and the distal end. The first lumen includes a first end located at least proximate the proximal end of the elongate shaft member and a second end located at least proximate the distal end of the elongate shaft member. In various embodiments, the distal end of the elongate member is arranged to be deliverable ahead of the proximal end of the elongate shaft member through a bodily opening leading to a bodily cavity, the length of the elongate shaft member sufficient to position the proximal end outside a body including the bodily cavity during a state in which the distal end is positioned in the bodily cavity. According to some embodiments, the flushing kit may be summarized as including a vessel including an interior cavity and a first port in fluid communication with the interior cavity. A first portion of the interior cavity is sized to receive at least a quantity of liquid sufficient to flush the first lumen of the elongate shaft member of a fluid other than the liquid. The first port is sized to removably receive a distal end portion of the elongate shaft member, the distal end portion of the elongate shaft member including the distal end of the elongate shaft member and the second end of the first lumen. According to various embodiments, the vessel includes a size too large for delivery through the bodily opening leading to the bodily cavity at least in a state in which the interior cavity is void of the liquid. According to various embodiments, the flushing kit includes a seal arranged to selectively seal an exterior surface of a first part of the distal end portion of the elongate shaft member to a portion of the vessel in a state in which at least a second part of the distal end portion of the elongate shaft member including the distal end of the elongate shaft member and the second end of the first lumen is positioned, via the first port, in the interior cavity at a location suitable to supply at least part of the liquid into the second end of the first lumen to flush the first lumen of the fluid other than the liquid in a direction through the first lumen extending from the second end of the first lumen toward the first end of the first lumen.

In some embodiments, the vessel may include a second port in fluid communication with the interior cavity, the second port arranged to fluidly communicate with a source of particular fluid other than the liquid and provide the particular fluid into a second portion of the interior cavity to pressurize the liquid in the first portion of the interior cavity. In various embodiments, the first port and the second port are different ports. In some embodiments, the second port may be arranged to avoid receiving the distal end portion of the elongate shaft member when the distal end portion of the elongate shaft member is received in the first port. In some embodiments, the second port may be positioned to permit a flow of the particular fluid from the second portion of the interior cavity through the second port while concurrently preventing a flow of the liquid from the first portion of the interior cavity through the second port at least during a state in which the liquid in the first portion of the interior cavity undergoes a reduction in pressure. In some embodiments, the vessel may be positionable to permit a flow of the particular fluid from the second portion of the interior cavity through the second port while concurrently preventing a flow of the liquid from the first portion of the interior cavity through the second port at least during a state in which the liquid in the first portion of the interior cavity undergoes a reduction in pressure.

In some embodiments, the vessel may include a conduit member arranged to fluidly communicate with the source of particular fluid, the conduit member including a first conduit end, a second conduit end and a second lumen extending between the first conduit end and the second conduit end. According to some embodiments, the first conduit end is arranged to receive the particular fluid from the source of particular fluid, and the second lumen is arranged to convey a flow of the particular fluid toward the second conduit end, the second conduit end being arranged to provide the particular fluid into the second portion of the interior cavity. In some embodiments, the second port may be provided by the second conduit end. In some embodiments, the conduit member may be arranged to locate the second conduit end at a location in the interior cavity away from the liquid in the first portion of the interior cavity. At least part of the conduit member may extend across at least part of the first portion of the interior cavity according to some embodiments.

In some embodiments, the conduit member may be arranged to locate the second conduit end in the second portion of the interior cavity. In some embodiments, the second lumen may be arranged to avoid receiving the distal end portion of the elongate shaft member when the distal end portion of the elongate shaft member is received in the first port. In some embodiments, the flushing kit may include a first valve coupled between the first conduit end of the conduit member and the source of particular fluid. According to some embodiments, the first valve may be selectively operable in a first state in which the particular fluid is allowed to flow via the conduit member from the source of particular fluid to the second portion of the interior cavity, and the first valve may be selectively operable in a second state in which the particular fluid is restricted from flowing via the conduit member from the source of particular fluid to the second portion of the interior cavity. In some embodiments, the first valve may be selectively operable in a third state in which the particular fluid is restricted from flowing via the conduit member from the source of particular fluid to the second portion of the interior cavity and the particular fluid is allowed to flow via the conduit from the second portion of the interior cavity to a particular location located away from the source of particular fluid, the particular location not located in the interior cavity and not located in the elongate shaft member. In some embodiments, the flushing kit may include a check valve operatively coupled between the source of particular fluid and the first valve to restrict at least a flow of the particular fluid from the first valve toward the source of particular fluid.

In some embodiments, the vessel may include a second port in fluid communication with the interior cavity, the second port configured to fluidly communicate with a particular fluid in a second portion of the interior cavity, the particular fluid being other than the liquid. In some embodiments, the first port and the second port are different ports. In some embodiments, the second port may be arranged to avoid receiving the distal end portion of the elongate shaft member when the distal end portion of the elongate shaft member is received in the first port. In some embodiments, the second port may be positioned to permit a flow of the particular fluid through the second port while concurrently preventing a flow of the liquid through the second port. In some embodiments, the vessel may be positionable to permit a flow of the particular fluid through the second port while concurrently preventing a flow of the liquid through the second port. In some embodiments, the vessel may include a wall portion between the first portion of the interior cavity and second portion of the interior cavity, at least part of the wall portion moveable to exert pressure on the liquid in the first portion of the interior cavity when the particular fluid is received in the second portion of the interior cavity.

In some embodiments, the vessel may include a conduit member arranged to fluidly communicate with the source of particular fluid, the conduit member including a first conduit end, a second conduit end and a second lumen extending between the first conduit end and the second conduit end. According to some embodiments, the first conduit end is arranged to receive the particular fluid from the source of particular fluid and the second lumen is arranged to convey a flow of the particular fluid toward the second conduit end, the second conduit end being arranged to provide the particular fluid into the second portion of the interior cavity. In some embodiments, the second port may be provided by the second conduit end. In some embodiments, the conduit member may be arranged to locate the second conduit end at a location in the interior cavity away from the liquid in the first portion of the interior cavity. In some embodiments, at least part of the conduit member may extend across at least part of the first portion of the interior cavity.

In some embodiments, the conduit member may be arranged to locate the second conduit end in the second portion of the interior cavity. In some embodiments, the second lumen may be arranged to avoid receiving the distal end portion of the elongate shaft member when the distal end portion of the elongate shaft member is received in the first port. In some embodiments, the flushing kit may include a first three-way valve operatively coupled between the second port and the source of particular fluid. In some embodiments, the flushing kit may include a check valve operatively coupled between the source of particular fluid and the first three-way valve to restrict at least a flow of the particular fluid from the first three-way valve toward the source of particular fluid. In some embodiments, the flushing kit may include a second three-way valve operatively coupled between the check valve and the source of particular fluid.

In some embodiments, a second portion of the interior cavity may be sized to receive at least a quantity of particular fluid other than the liquid, the quantity of particular fluid being sufficient to exert pressure on the liquid in the first portion of the interior cavity, the pressure sufficient to cause movement of at least some of the liquid in the first portion of the interior cavity into the second end of the first lumen and flush the first lumen of the fluid other than the liquid in the direction through the first lumen extending from the second end of the first lumen toward the first end of the first lumen.

In some embodiments, the vessel may be sized too large to be percutaneously delivered through the bodily opening leading to the bodily cavity at least in the state in which the first portion of the interior cavity is void of the liquid.

In some embodiments, the vessel may include a removable cap, the cap removable to provide access to the interior cavity. In some embodiments, the first port may be provided in the cap. In some embodiments, a second portion of the interior cavity may be sized to contain at least a quantity of particular fluid other than the liquid concurrently with the liquid received in the first portion of the interior cavity. In some embodiments, the vessel may include a second port in fluid communication with the interior cavity, the second port positioned to permit a flow of the particular fluid through the second port while concurrently preventing a flow of the liquid through the second port. In various embodiments, the first port and the second port are different ports provided in the cap.

In some embodiments, the vessel may include a size too large to fit in the bodily cavity at least in the state in which the first portion of the interior cavity is void of the liquid. In some embodiments, the exterior surface of the first part of the distal end portion of the elongate shaft member may be a cylindrical surface. In some embodiments, the portion of the vessel may be an engagement surface of the seal. In some embodiments, the engagement surface of the seal is a radially-inward-facing surface. In some embodiments, the engagement surface is a circumferential surface.

In some embodiments, the catheter includes a manipulable portion physically coupled to the distal end portion of the elongate shaft member, the manipulable portion being selectively moveable between a delivery configuration and a deployed configuration, a size of the manipulable portion in the deployed configuration being larger than a corresponding size of the manipulable portion in the deployed configuration. In some embodiments, the first port is sized to permit delivery of the manipulable portion through the first port when the manipulable portion is in the delivery configuration. In some embodiments, the first port is sized to restrict delivery of the manipulable portion through the first port when the manipulable portion is in the deployed configuration. In some embodiments, a volume of the first portion of the interior cavity may be greater than a volume encompassed by the manipulable portion when the manipulable portion is in the deployed configuration.

In some embodiments, the catheter includes a manipulable portion physically coupled to the distal end portion of the elongate shaft member, the manipulable portion being selectively moveable between a delivery configuration in which the manipulable portion is sized to permit delivery of the manipulable portion through the bodily opening leading to the bodily cavity and a deployed configuration in which the manipulable portion is sized too large to permit delivery of the manipulable portion through the bodily opening leading to the bodily cavity. According to some embodiments, a volume of the first portion of the interior cavity may be greater than a volume encompassed by the manipulable portion when the manipulable portion is in the deployed configuration.

Various flushing kits may include combinations and subset of those summarized above.

In some embodiments, a catheter is provided, the catheter including an elongate shaft member that includes a proximal end, a distal end, a length from the proximal end to the distal end, and at least a first lumen extending between the proximal end and the distal end. The first lumen includes a first end located at least proximate the proximal end of the elongate shaft member and a second end located at least proximate the distal end of the elongate shaft member. According to various embodiments, the distal end of the elongate shaft member is arranged to be deliverable ahead of the proximal end of the elongate shaft member through a bodily opening leading to a bodily cavity. According to various embodiments, the length of the elongate shaft member is sufficient to position the proximal end outside a body that includes the bodily cavity during a state in which the distal end is positioned in the bodily cavity. According to various embodiments, a method for flushing the catheter may be summarized as including providing a quantity of liquid into at least a first portion of an interior cavity of a vessel. According to various embodiments, the method includes inserting at least part of a distal end portion of the elongate shaft member including the distal end of the elongate shaft member and the second end of the first lumen into the interior cavity via a first port provided by the vessel, the second end of the first lumen in fluid communication with the liquid provided in the first portion of the interior cavity. According to various embodiments, the method includes establishing a flow of at least some of the liquid in the first portion of the interior cavity through the first lumen from the second end of the first lumen toward the first end of the first lumen to flush a fluid other than the liquid from the first lumen.

In some embodiments, the method may include removing the at least part of the distal end portion of the elongate shaft member from the interior cavity prior to a delivery of at least part of the catheter through the bodily opening leading to the bodily cavity. In some embodiments, the method may include removing the at least part of the distal end portion of the elongate shaft member from the interior cavity prior to a delivery of at least the distal end portion of the elongate shaft member through the bodily opening leading to the bodily cavity. In some embodiments, the vessel includes a size too large for delivery of the vessel through the bodily opening leading to the bodily cavity at least in a state in which the first portion of the interior cavity is void of the liquid.

In some embodiments, the liquid in at least the first portion of the interior cavity is pressurized. In some embodiments, the method may include pressurizing the liquid in at least the first portion of the interior cavity after the liquid is provided in the first portion of the interior cavity. In some embodiments, the method may include pressurizing the liquid in at least the first portion of the interior cavity of the chamber to establish the flow of at least some of the liquid in the first portion of the interior cavity through the first lumen from the second end of the first lumen toward the first end of the first lumen to flush the fluid other than the liquid from the first lumen.

In some embodiments, the method may include providing a particular fluid into a second portion of the interior cavity to pressurize the liquid provided in the first portion of the interior cavity. In some embodiments, the particular fluid is different than the liquid.

In some embodiments, the method may include providing a quantity of particular fluid other than the liquid into a second portion of the interior cavity while at least some of the liquid is in the first portion of the interior cavity. In some embodiments, the vessel may include a second port in fluid communication with the interior cavity, the second port other than the first port, and at least some of the quantity of particular fluid may be provided into the second portion of the interior cavity at least through the second port. In some embodiments, the second port may be arranged to prevent any reception of the distal end portion of the elongate shaft member when the distal end portion of the elongate shaft member is inserted into the interior cavity via the first port. In some embodiments, the second port is positionable to permit a flow of the particular fluid through the second port while concurrently preventing a flow of the liquid through the second port.

In some embodiments, the method may include providing a quantity of particular fluid other than the liquid into a second portion of the interior cavity, the quantity of particular fluid being sufficient to exert pressure on the liquid in the first portion of the interior cavity, the pressure sufficient to cause the establishing the flow of the at least some of the liquid in the first portion of the interior cavity through the first lumen from the second end of the first lumen toward the first end of the first lumen to flush the fluid other than the liquid from the first lumen. In some embodiments, the method may include providing the quantity of particular fluid other than the liquid into the second portion of the interior cavity after the quantity of liquid has been provided into at least the first portion of the interior cavity.

In some embodiments, the method may include providing a quantity of particular fluid other than the liquid into a second portion of the interior cavity after the quantity of liquid has been provided into at least the first portion of the interior cavity.

In some embodiments, the method may include providing a quantity of particular fluid other than the liquid into a second portion of the interior cavity while at least some of the liquid is in the first portion of the interior cavity. In some embodiments, the vessel may include a second port in fluid communication with the interior cavity, the second port other than the first port, and at least some of the quantity of particular fluid being provided into the second portion of the interior cavity at least through the second port. In some embodiments, the vessel may include a wall portion, and the method includes moving at least part of the wall portion to exert pressure on the liquid in the first portion of the interior cavity, the pressure sufficient to cause the establishing the flow of the at least some of the liquid in the first portion of the interior cavity through the first lumen from the second end of the first lumen toward the first end of the first lumen to flush the fluid other than the liquid from the first lumen. In some embodiments, the wall portion may be provided between the first portion of the interior cavity and the second portion of the interior cavity.

In some embodiments, the method may include providing a quantity of particular fluid other than the liquid into a second portion of the interior cavity while at least some of the liquid is in the first portion of the interior cavity. In some embodiments, the vessel may include a conduit member that includes a first conduit end, a second conduit end, and a second lumen extending between the first conduit end and the second conduit end. According to some embodiments, the method may include conveying a flow of the particular fluid though the second lumen toward the second conduit end, the second conduit end being arranged to provide at least some of the quantity of particular fluid into the second portion of the interior cavity. In some embodiments, the conduit member may be arranged to locate the second conduit end at a location in the interior cavity away from the liquid provided in the first portion of the interior cavity. In some embodiments, at least part of the conduit member may extend across at least part of the first portion of the interior cavity. In some embodiments, the conduit member may be arranged to locate the second conduit end in the second portion of the interior cavity. In some embodiments, the second lumen may be arranged to prevent any reception of the distal end portion of the elongate shaft member when the distal end portion of the elongate shaft member is inserted into the interior cavity via the first port. In some embodiments, the quantity of particular fluid is sufficient to exert pressure on the liquid, and the pressure sufficient to cause the establishing the flow of the at least some of the liquid in the first portion of the interior cavity through the first lumen from the second end of the first lumen toward the first end of the first lumen to flush the fluid other than the liquid from the first lumen.

In some embodiments, the method may include providing a quantity of particular fluid other than the liquid into a second portion of the interior cavity while at least some of the liquid is in the first portion of the interior cavity. In some embodiments, the vessel may include a second port in fluid communication with the interior cavity, the second port other than the first port, and at least some of the quantity of particular fluid being provided into the second portion of the interior cavity at least through the second port. In some embodiments, the vessel may include a removable cap, the cap removable to provide access to the interior cavity and wherein both the first port and the second port are provided in the cap.

In some embodiments, the vessel may include a removable cap, the cap removable to provide access to the interior cavity and wherein the first port is provided in the cap.

In some embodiments, the method may include manipulating a seal member to seal an exterior surface of the distal end portion of the elongate shaft member to at least part of the vessel, and subsequently, manipulating the seal member to unseal the exterior surface of the distal end portion of the elongate shaft member from the at least part of the vessel at least prior to a delivery of at least the distal end portion of the elongate shaft member through the bodily opening leading to the bodily cavity. In some embodiments, the method may include pressurizing the liquid in the first portion of the interior cavity after the manipulating the seal member to seal an exterior surface of the distal end portion of the elongate shaft member to the at least part of the vessel but before the manipulating the seal member to unseal the exterior surface of the distal end portion of the elongate shaft member from the at least part of the vessel.

In some embodiments, the catheter comprises a manipulable portion physically coupled to the distal end portion of the elongate shaft member, the manipulable portion selectively moveable from an unexpanded configuration in which the manipulable portion is sized for delivery through the first port and an expanded configuration in which the manipulable portion is sized too large for delivery through the first port, and wherein the method comprises delivering the manipulable portion in the unexpanded configuration via the first port into the first portion of the interior cavity. In some embodiments, the method may include moving the manipulable portion from the unexpanded configuration to the expanded configuration in the first portion of the interior cavity. In some embodiments, the method may include repeatedly moving the manipulable portion, when the manipulable portion is in the expanded configuration in the first portion of the interior cavity to agitate the liquid in the first portion of the interior cavity. In some embodiments, the method may include moving the manipulable portion from the unexpanded configuration to the expanded configuration while the manipulable portion is wetted by the liquid provided in the first portion of the interior cavity.

In some embodiments, the method may include pressurizing the liquid in at least the first portion of the interior cavity after the liquid is provided in the first portion of the interior cavity to prevent fluid flow from the first lumen into the interior cavity.

In some embodiments, the method may include providing a particular fluid into a second portion of the interior cavity to pressurize the liquid provided in the first portion of the interior cavity. In some embodiments, the providing the particular fluid into the second portion of the interior cavity to pressurize the liquid in the first portion of the interior cavity may include providing the particular fluid into the second portion of the interior cavity via a second port provided by the vessel. According to some embodiments, the method may include removing at least some of the particular fluid from the second portion of the interior cavity to depressurize the liquid in the first portion of the interior cavity, the at least some of the particular fluid removed from the second portion of the interior cavity via a third port provided by the vessel, each of the second and the third port being other than the first port. In some embodiments, the third port may be provided by the second port.

Various methods can include combinations and subsets of those summarized above.

Various embodiments of the present invention may include systems, devices, or machines that are or include combinations or subsets of any or all of the systems, devices, or machines and associated features thereof described herein.

Further, all or part of any or all of the systems, devices, or machines discussed herein or combinations or subcombinations thereof may implement or execute all or part of any or all of the methods discussed herein or combinations or subcombinations thereof. Further, any or all of the methods and associated features thereof discussed herein may be implemented or executed by all or part of a device system, apparatus, or machine, such as all or a part of any of the systems, apparatuses, or machines described herein or a combination or subcombination thereof.

BRIEF DESCRIPTION OF THE DRAWINGS

It is to be understood that the attached drawings are for purposes of illustrating aspects of various embodiments and may include elements that are not to scale.

FIG. 8D is a block diagram of a method for providing a quantity of particular fluid into a portion of an interior cavity of a vessel of the flushing kit, according to some example embodiments.

DETAILED DESCRIPTION

Figure 1:
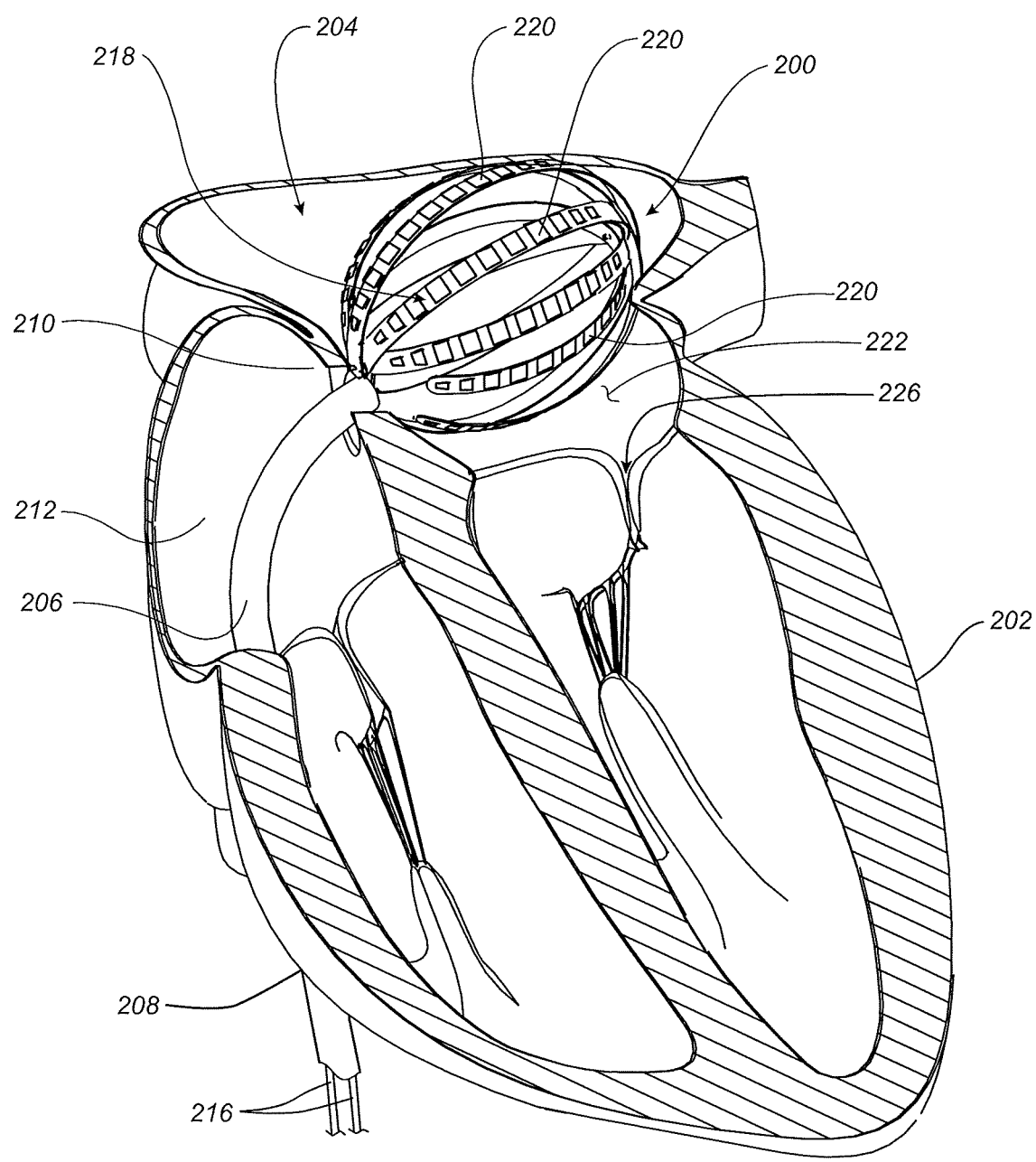
FIG. 1 is a cutaway diagram of a heart showing a transducer-based device percutaneously delivered to a left atrium of the heart, according to some example embodiments.

Various embodiments of the present invention address the above-discussed need and provide technical solutions in the art with inventive medical device flushing systems and methods. In some embodiments, such systems and methods include inserting a distal end portion of an elongate shaft member of a catheter into liquid within a vessel. In some embodiments, the liquid is pressurized, which causes the liquid to flow into a lumen of the elongate shaft member from the distal end of the elongate shaft member at least toward the proximal end of the elongate shaft member to flush undesirable fluid (e.g., air) from the lumen, in contrast to conventional proximal-end-to-distal-end flushing schemes. Distal-end-toward-proximal-end flushing can be more beneficial than conventional proximal-end-to-distal-end flushing schemes, at least because it becomes possible to impart higher flow rates in the flushing liquid thereby increasing the flushing efficacy according to some embodiments. In some embodiments, while the distal end portion of the elongate shaft member is inserted in the liquid in the vessel, a manipulable portion of the catheter system is manipulated (e.g., expanded and contracted or otherwise manipulated) within the liquid to flush or otherwise remove undesired fluid therefrom, which is another benefit of distal-end-toward-proximal-end flushing, as it allows the manipulable portion to be cleansed of undesired fluid along with the lumen of the elongate member. In some embodiments, the distal end portion of the elongate shaft member of the catheter is inserted into the liquid within the vessel while at least the elongate shaft member is in a substantially horizontal orientation, which can be more beneficial than conventional vertical flushing orientations at least because the horizontal flushing arrangement is easier to physically handle. It should be noted that the invention is not limited to these or any other examples provided herein, which are referred to for purposes of illustration only.

In this regard, in the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In addition, unless otherwise explicitly noted or required by context, the word "subset" is intended to mean a set having the same or fewer elements of those present in the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least on A' includes A as well as the possibility of one or more other additional elements besides A. In the same manner, the phrase 'based on A' includes A, as well as the possibility of one or more other additional elements besides A. However, the phrase 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, or device system resides across different housings. The word "device" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

In some embodiments, the term "adjacent", the term "proximate", and the like refer at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refers to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", and the like additionally or alternatively refers to at least a sufficient closeness between the objects defined as adjacent, proximate, and the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments.

The word "ablation" as used in this disclosure should be understood to include, for example, any disruption to certain properties of tissue. Most commonly, the disruption is to the electrical conductivity and is achieved by heating, which can be generated with resistive or radio-frequency (RF) techniques for example. However, any other technique for such disruption may be included when the term "ablation" is used, such as mechanical, chemical, electroporation or optical techniques.

The word "fluid", as used in this disclosure, should be understood to include, for example, liquid or gas.

The phrase "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The phrase "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

The word "tissue" as used in some embodiments in this disclosure should be understood to include, for example, any surface-forming tissue that is used to form a surface of a body or a surface within a bodily cavity, a surface of an anatomical feature or a surface of a feature associated with a bodily opening positioned in fluid communication with the bodily cavity. The tissue can include, for example, part or all of a tissue wall or membrane that defines a surface of the bodily cavity. In this regard, the tissue can form an interior surface of the cavity that surrounds a fluid within the cavity. In the case of cardiac applications, tissue can include, for example, tissue used to form an interior surface of an intra-cardiac cavity such as a left atrium or right atrium. In some embodiments, tissue is non-excised tissue. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include, for example, an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed.

The term "activation" as used in this disclosure should be interpreted broadly as making active a particular function as related to various transducers disclosed in this disclosure. Particular functions can include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer is activated to cause a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used. For example, in some embodiments, activation initiation may cause initiation of a transmission of energy (e.g., energy sufficient for tissue ablation) from a particular transducer or electrode.

The phrase "physically coupled" is intended to include, in some embodiments, a coupling between two objects that involves a coupling between the two objects where the two objects physical contact each other at least in one state of the coupling between the two objects. The phrases "fixedly coupled", "permanently coupled", and the like, are intended to include, in some embodiments, a secure coupling between two objects that, in some embodiments, does not involve or include a mechanism configured to release the coupling of the two objects. The phrases "removably coupled", "detachably coupled", and the like, are intended to include, in some embodiments, a coupling between two objects that, in some embodiments, allows such coupling to be repeatedly disengaged and re-engaged without damaging the coupling (if a distinct coupling mechanism exists, e.g., in contrast to an interference fit that relies on friction), without damaging either or both of the objects, or without damaging the coupling (if a distinct coupling mechanism exists) and without damaging either or both of the objects. The phrase "operatively coupled" is intended to include, for example, a coupling between two objects that transmits force, energy, information, or other influence at least from one of the two objects to the other of the two objects. An operative coupling does not exclude the possibility of a physical or fixed coupling in addition to the operative coupling. Unless otherwise explicitly noted or required by context, for any connection or coupling, direct or indirect, between components, devices, or other physical objects described herein, different embodiments include different ones of the above-described coupling types for such components, devices, or other physical objects. For example, unless otherwise explicitly noted or required by context, if a first physical object is shown in the figures or described in this text as being connected or coupled, directly or indirectly, to a second physical object, some embodiments will have the first physical object fixedly coupled to the second physical object; other embodiments will have the first physical object permanently coupled to the second physical object; other embodiments will have the first physical object removably or detachably coupled to the second physical object; other embodiments will have the first physical object not fixedly or permanently coupled to the second physical object while having the first physical object physically coupled to the second physical object; other embodiments will have the first physical object not physically coupled or fixedly coupled to the second physical object, but will have the first physical object operatively coupled to the second physical object; etc.

In some embodiments, the phrases "fluid communication", "fluidly communicate", "fluidly coupled", and the like, are intended to include, for example, a port or opening, of a physical object leading to a lumen or other internal cavity, where the port, opening, lumen, or internal cavity leads to body (e.g., a source or drain) of a first fluid, such that (a) at least some of the first fluid moves or is able to move through (1) the port or opening into the lumen or other internal cavity, (2) the lumen or other internal cavity into the port or opening, or both (a)(1) and (a)(2); (b) at least some of a second fluid moves or is able to move through (1) the lumen or other internal cavity into the port or opening, (2) the port or opening into the lumen or other internal cavity, or both (b)(1) and (b)(2); or both (a) and (b). In some embodiments, the first fluid and the second fluid are the same. In some embodiments, the first fluid and the second fluid are different.

Various embodiments of catheter systems or catheter device systems are described herein. It should be noted that any catheter system described herein may also be referred to as a medical system or medical device system. Some of the described devices of such systems are medical devices that are percutaneously or intravascularly deployed. Some of the described devices are deployed through a bodily opening that is accessible without puncturing, cutting or otherwise perforating bodily tissue to create an access to the bodily opening. Some of the described devices employ transducer-based devices or device systems. Some of the described devices are moveable between a delivery or unexpanded configuration in which a portion of the device is sized, shaped, or both for passage through a bodily opening leading to a bodily cavity, and an expanded or deployed configuration in which the portion of the device has a size, shape, or both too large for passage through the bodily opening leading to the bodily cavity. An example of an expanded or deployed configuration is when the portion of the catheter system is in its intended-deployed-operational state inside the bodily cavity. Another example of the expanded or deployed configuration is when the portion of the catheter system is being changed from the delivery configuration to the intended-deployed-operational state to a point where the portion of the device now has a size, shape, or both too large for passage through the bodily opening leading to the bodily cavity. In some embodiments, at least a portion of at least one of the described devices has a dimension or size that is smaller in the delivery or unexpanded configuration than a corresponding dimension or size of the at least a portion of at least one of the described devices in the expanded or deployed configuration.

In some example embodiments, the catheter system includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical device system to map the cavity, for example using positions of openings or ports into and out of the cavity to determine a position or orientation (i.e., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

FIG. 1 shows a portion of a catheter system, according to some embodiments, such portion including a transducer-based device 200, which may be at least part of a medical device useful in investigating or treating a bodily organ, for example, a heart 202, according to some example embodiments. The transducer-based device 200 may also be referred to as a manipulable portion, due to its ability to have its size, shape, or both size and shape altered, according to some embodiments described below. Transducer-based device 200 can be percutaneously or intravascularly inserted into a portion of the heart 202, such as an intra-cardiac cavity like left atrium 204. The components of the transducer-based device 200 (as well as the transducer-based device 300, the catheter system 500, and the kit 600, described below) may be sterile.

In the example of FIG. 1, the illustrated portion of the catheter system also includes a catheter 206, which may be inserted via the inferior vena cava 208 and may penetrate through a bodily opening in transatrial septum 210 from right atrium 212. In other embodiments, other paths may be taken.

Catheter 206 includes an elongated flexible rod or elongated shaft member appropriately sized to be delivered percutaneously or intravascularly. Various portions of catheter 206 may be steerable. Catheter 206 may include one or more lumens, for example within the elongated shaft member. The lumen(s) may carry one or more communications or power paths, or both. For example, the lumens(s) may carry one or more electrical conductors 216 (two shown in this embodiment). Electrical conductors 216 provide electrical connections to transducer-based device 200 that are accessible externally from a patient in which the transducer-based device 200 is inserted. The lumen(s) may carry various control elements (e.g., control lines) operatively coupling one or more actuators to a manipulable portion (e.g., manipulable portion 200)

In various embodiments, transducer-based device, or manipulable portion, 200 includes a frame or structure 218, which assumes an unexpanded configuration for delivery to left atrium 204. Structure 218 is expanded (i.e., shown in a deployed or expanded configuration in FIG. 1) upon delivery to left atrium 204 to position a plurality of transducers 220 (three called out in FIG. 1) proximate the interior surface formed by tissue 222 of left atrium 204. In this regard, it can be stated that one or more of the transducers 220 are moveable with one or more parts of the transducer-based device, or manipulable portion, 200. In some embodiments, at least some of the transducers 220 are used to sense a physical characteristic of a fluid (i.e., blood) or tissue 222, or both, that may be used to determine a position or orientation (i.e., pose), or both, of a portion of transducer-based device 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern or path around various ones of the bodily openings, ports or pulmonary vein ostia, for instance to reduce or eliminate the occurrence of atrial fibrillation.

Figure 2A:
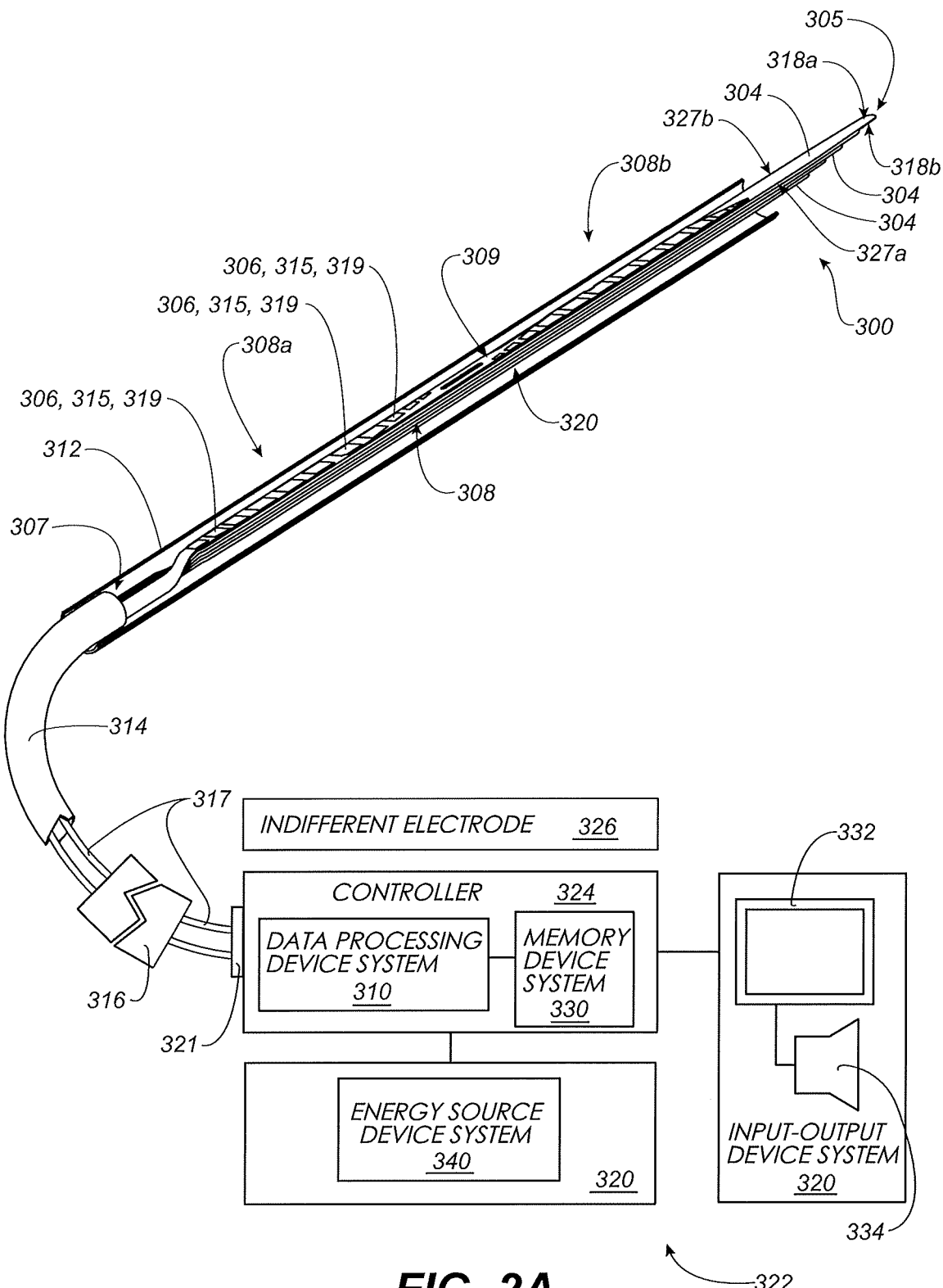
FIG. 2A is a partially schematic representation of a catheter system, according to some example embodiments, the system, which may also be referred to as a medical system, including a data processing device system, an input-output device system, a processor-accessible memory device system, and a manipulable portion shown in a delivery or unexpanded configuration.
Figure 2B:
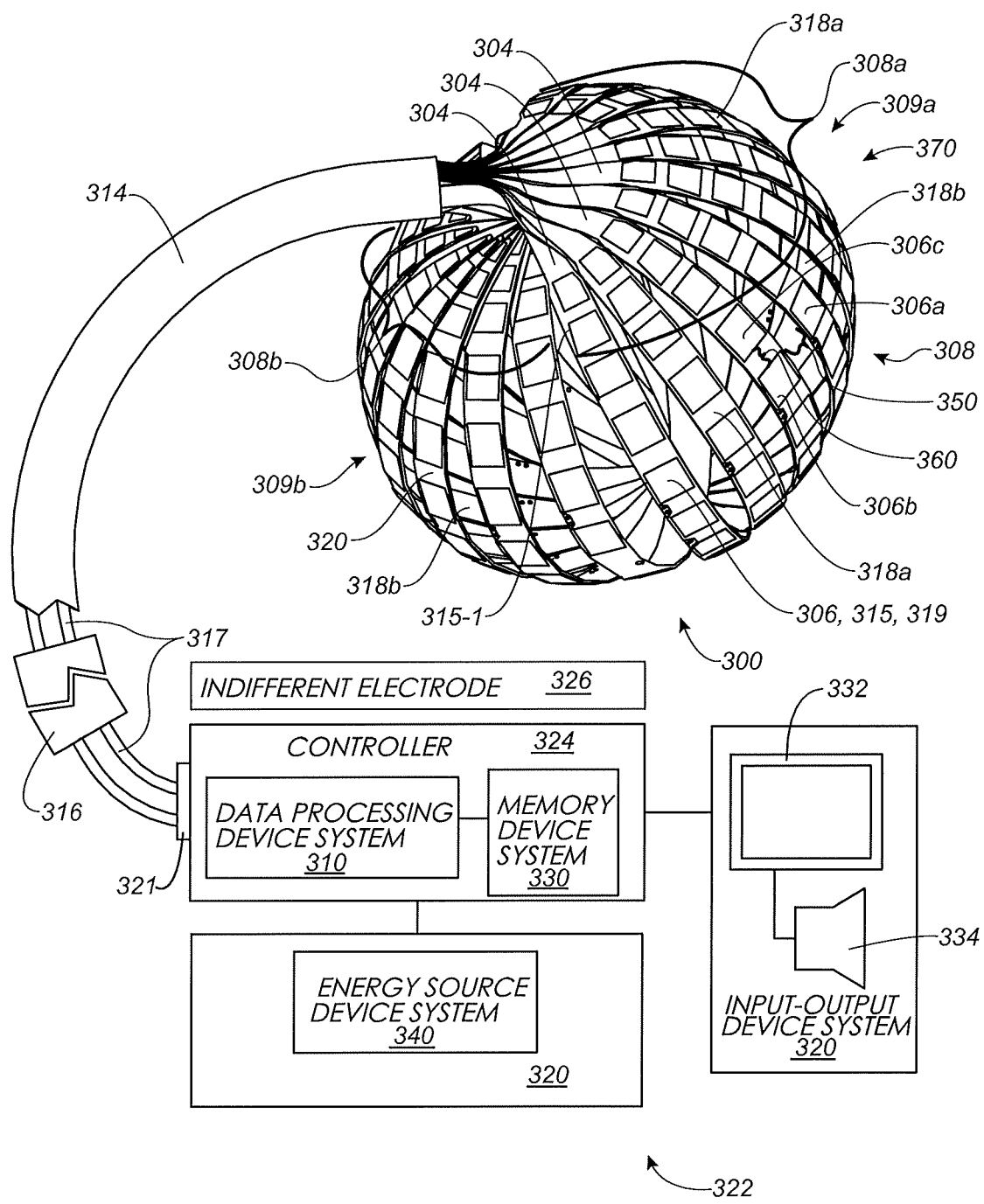
FIG. 2B is the catheter system of FIG. 2A with the manipulable portion shown in a deployed or expanded configuration, according to some example embodiments.

FIGS. 2A and 2B show a catheter system (i.e., a portion thereof shown schematically) that includes a transducer-based device 300 according to one illustrated embodiment. The transducer-based device 300 may correspond to the transducer-based device 200 and, in this regard, may also be referred to as a manipulable portion, due to its ability to have its size, shape, or both size and shape altered, according to some embodiments described below. Transducer-based device 300 may include a plurality of elongate members 304 (three called out in each of FIGS. 2A and 2B) and a plurality of transducers 306 (three called out in FIG. 2A, and three called out in FIG. 2B as 306a, 306b, and 306c). As will become apparent, the plurality of transducers 306 is positionable within a bodily cavity. For example, in some embodiments, the transducers 306 can be positioned in a bodily cavity by movement into, within, or into and within the bodily cavity, with or without a change in a particular configuration of the plurality of transducers 306. In some embodiments, the plurality of transducers 306 are arrangeable to form a two- or three-dimensional distribution, grid or array of the transducers capable of mapping, ablating, or stimulating an inside surface of a bodily cavity or lumen without requiring mechanical scanning. As shown, for example, in FIG. 2A, the plurality of transducers 306 are arranged in a distribution receivable in a bodily cavity, as the transducer-based device 300 and its plurality of transducers 306 are located within the catheter sheath 312. Stated differently, in FIG. 2A, for example, the plurality of transducers 306 are arranged in a distribution suitable for delivery to a bodily cavity. (It should also be noted, however, that the expanded or deployed configuration (e.g., FIGS. 1, 2B, 4A, 6B) may also be considered to have the transducers 306 arranged in a distribution receivable in a bodily cavity, as the transducer-based device 300 and its transducers 306 may be returned to the delivery configuration of FIGS. 2A, 4B for example). In some embodiments, each of the transducers 306 includes an electrode 315 (one called out in FIG. 2B) having an energy transmission surface 319 (one called out in FIG. 2B) suitable for transmitting energy in various directions. In some embodiments, tissue-ablating energy is transmitted toward or away from an electrode 315. In some embodiments, tissue-based electrophysiological energy is transmitted toward an electrode 315.

The elongate members 304 form part of a manipulable portion, and in various embodiments, are arranged in a frame or structure 308 that is selectively moveable between an unexpanded or delivery configuration (i.e., as shown in FIG. 2A) and an expanded or deployed configuration (i.e., as shown in FIG. 2B) that may be used to position elongate members 304 against a tissue surface within the bodily cavity or position the elongate members 304 in the vicinity of or in contact with the tissue surface. In this regard, it may also be stated that the transducer-based device, or manipulable portion, 300 is selectively moveable between an unexpanded or delivery configuration (i.e., as shown in FIG. 2A) and an expanded or deployed configuration (i.e., as shown in FIG. 2B). In some embodiments, the transducer-based device, or manipulable portion, 300, (e.g., the structure 308 thereof) has a size, shape, or both a size and a shape in the unexpanded or delivery configuration suitable for percutaneous delivery through a bodily opening (for example, via an elongate shaft member such as catheter sheath 312, not shown in FIG. 2B) to the bodily cavity. In some embodiments, structure 308 has a size, shape, or both a size and a shape in the expanded or deployed configuration too large for percutaneous delivery through a bodily opening (i.e., via catheter sheath 312) to the bodily cavity. The elongate members 304 may form part of a flexible circuit structure (i.e., also known as a flexible printed circuit board (PCB)). The elongate members 304 may include a plurality of different material layers, and each of the elongate members 304 may include a plurality of different material layers. The structure 308 may include a shape memory material, for instance Nitinol. The structure 308 may include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. The number of elongate members depicted in FIG. 2B is non-limiting.

Figure 3:
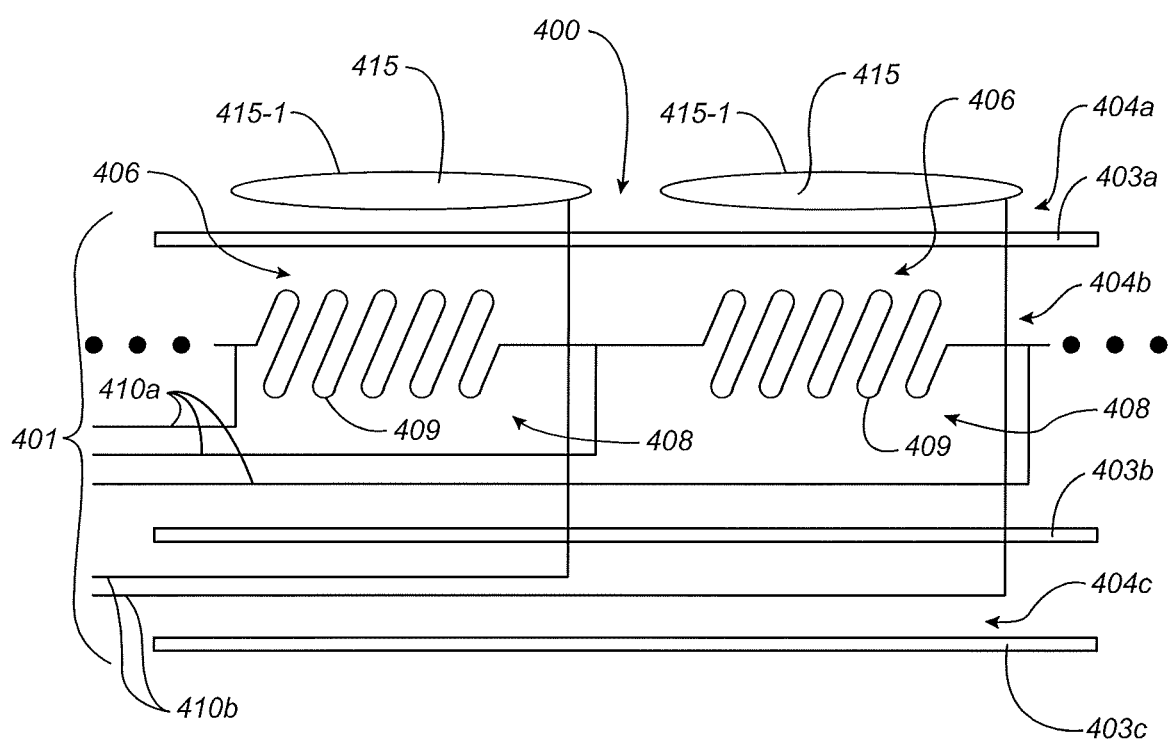
FIG. 3 is a schematic representation of a transducer-based device that includes a flexible circuit structure, according to some example embodiments.

FIG. 3 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively moveable between an unexpanded or delivery configuration sized for percutaneous delivery and an expanded or deployed configuration sized too large for percutaneous delivery. In some embodiments, the flexible circuit structure 401 may be located on, or form at least part of, of a structural component (e.g., elongate member 304) of a transducer-based device system.

The flexible circuit structure 401 may be formed by various techniques including flexible printed circuit techniques. In some embodiments, the flexible circuit structure 401 includes various layers including flexible layers 403*a*, 403*b*, and 403*c* (i.e., collectively flexible layers 403). In some embodiments, each of flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404*a*, 404*b*, and 404*c* (collectively electrically conductive layers 404) that are interleaved with the flexible layers 403. In some embodiments, each of the electrically conductive layers 404 is patterned to form various electrically conductive elements. For example, electrically conductive layer 404*a* is patterned to form a respective electrode 415 of each of the transducers 406. Electrodes 415 have respective electrode edges 415-1 that form a periphery of an electrically conductive surface associated with the respective electrode 415. FIG. 2B shows another example of electrode edges 315-1 and illustrates that the electrode edges can define electrically conductive surface peripheries of various shapes.

Returning to FIG. 3, electrically conductive layer 404*b* is patterned, in some embodiments, to form respective temperature sensors 408 for each of the transducers 406 as well as various leads 410*a* arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404*c* is patterned to provide portions of various leads 410*b* arranged to provide an electrical communication path to electrodes 415. In some embodiments, leads 410*b* are arranged to pass though vias in flexible layers 403*a* and 403*b* to connect with electrodes 415. Although FIG. 3 shows flexible layer 403*c* as being a bottom-most layer, some embodiments may include one or more additional layers underneath flexible layer 403*c*, such as one or more structural layers, such as a steel or composite layer. These one or more structural layers, in some embodiments, are part of the flexible circuit structure 401 and may be part of, e.g., elongate member 304. In addition, although FIG. 3 shows only three flexible layers 403*a*-403*c* and only three electrically conductive layers 404*a*-404*c*, it should be noted that other numbers of flexible layers, other numbers of electrically conductive layers, or both, may be included.

In some embodiments, electrodes 415 are employed to selectively deliver RF energy to various tissue structures within a bodily cavity (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example.

Energy that is sufficient for tissue ablation may be dependent upon factors including tissue characteristics, transducer location, size, shape, relationship with respect to another transducer or a bodily cavity, material or lack thereof between transducers, etc.

In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form at least part of a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). In some embodiments in which the transducer-based device is deployed in a bodily cavity (e.g., when the transducer-based device 300 is part of a catheter system and may be arranged to be percutaneously or intravascularly delivered to a bodily cavity via a catheter), it may be desirable to perform various mapping procedures in the bodily cavity. For example, when the bodily cavity is an intra-cardiac cavity, a desired mapping procedure may include mapping electrophysiological activity in the intra-cardiac cavity. Other desired mapping procedures may include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

Referring to FIGS. 2A, 2B, transducer-based device or manipulable portion 300 may communicate with, receive power from, or be controlled by a control system 322. In some embodiments, elongate members 304 may form a portion of an elongated cable 316 of control leads 317, for example by stacking multiple layers, and terminating at a connector 321 or other interface with control system 322. The control leads 317 may correspond to the electrical connectors 216 in FIG. 1 in some embodiments. The control system 322 may include a controller 324 that may include a data processing device system 310 and a memory device system 330 that stores data and instructions that are executable by the data processing device system 310 to process information received from transducer-based device 300 or to control operation of transducer-based device 300, for example activating various selected transducers 306 to ablate tissue. Controller 324 may include one or more controllers.

In some embodiments, the controller 324 may be configured to control deployment, expansion, retraction, or other manipulations of the shape, positioning, or both shape and positioning of the transducer-based device (e.g., manipulable portion) 300 at least by driving (e.g., by an electric or other motor) movement of various actuators or other catheter system components. In this regard, in some embodiments, the controller 324 is at least part of a control system, which may include one or more actuators, configured to advance at least part of the transducer-based device (e.g., 200, 300, 400, or 502), at least a portion of which may be considered a manipulable portion, out of the catheter sheath 312, retract at least part of the transducer-based device back into the catheter sheath 312, expand, contract, or otherwise change at least part of the shape of the transducer-based device.

Control system 322 may include an input-output device system 320 communicatively connected to the data processing device system 310 (i.e., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a health care provider or technician. For example, output from a mapping process may be displayed on a display device system 332.

Control system 322 may also include an energy source device system 340 including one or more energy source devices connected to transducers 306. In this regard, although FIG. 2A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through elongate shaft member 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 may be fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include as its energy source devices various electrical current sources or electrical power sources. In some embodiments, an indifferent electrode 326 is provided to receive at least a portion of the energy transmitted by at least some of the transducers 306. Consequently, although not shown in FIG. 2A, the indifferent electrode 326 may be communicatively connected to the energy source device system 340 via one or more communication lines in some embodiments. In addition, although shown separately in FIG. 2A, indifferent electrode 326 may be considered part of the energy source device system 340 in some embodiments. In some embodiments, the indifferent electrode 326 is provided outside the body or at least the bodily cavity in which the transducer-based device (e.g., 200, 300, 400, or 502) or catheter system 500 is, at least in part, located.

In some embodiments, the energy source device system 340 may include one or more driving motors configured to drive movement, in response to instructions from the controller 324, of various actuators or other catheter system components to control deployment, expansion, retraction, or other manipulations of the shape, positioning, or both shape and positioning of the transducer-based device (e.g., manipulable portion) 300.

It is understood that input-output device system 320 may include other systems. In some embodiments, input-output device system 320 may optionally include energy source device system 340, transducer-based device 300 or both energy source device system 340 and transducer-based device 300 by way of non-limiting example.

Structure 308 of transducer-based device 300 may be delivered and retrieved through a catheter member, for example, a catheter sheath 312. In some embodiments, the structure 308 provides expansion and contraction capabilities for a portion of a medical device (e.g., an arrangement, distribution or array of transducers 306). The transducers 306 may form part of, be positioned or located on, mounted or otherwise carried on the structure and the structure may be configurable to be appropriately sized to slide within a lumen of catheter sheath 312 in order to be deployed percutaneously or intravascularly. FIG. 2A shows one embodiment of such a structure. In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In various embodiments, the intermediate portion 309 of each of the elongate members 304 includes a respective pair of side edges of the front surface 318a, the back surface 318b, or both the front surface 318a and the back surface 318b, the side edges of each pair of side edges opposite to one another, the side edges of each pair of side edges extending between the proximal end 307 and the distal end 305 of the respective elongate member 304. In some embodiments, each pair of side edges includes a first side edge 327a (only one called out in FIG. 2A) and a second side edge 327b (only one called out in FIG. 2A). In some embodiments, each of the elongate members 304, including each respective intermediate portion 309, is arranged front surface 318a-toward-back surface 318b in a stacked array during an unexpanded or delivery configuration (e.g., FIG. 2A, 5B). In many cases, a stacked array allows the structure 308 to have a suitable size for percutaneous or intravascular delivery. A stacked array can allow structure 308 to have a spatially efficient size for delivery through a lumen of catheter sheath 312. In some embodiments, the elongate members 304 are arranged to be introduced into a bodily cavity distal end 305 first. For clarity, not all of the elongate members 304 of structure 308 are shown in FIG. 2A. A flexible catheter body or elongate shaft member 314 is used to deliver structure 308 through catheter sheath 312. In some embodiments, each elongate member includes a twisted portion proximate proximal end 307 (e.g., also FIG. 4B, discussed below).

In some embodiments, each of the elongate members 304 is arranged in a fanned arrangement 370 in FIG. 2B. In some embodiments, the fanned arrangement 370 is formed during the expanded or deployed configuration in which the transducer-based device (e.g., manipulable portion) 300 or structure 308 thereof is manipulated to have a size, shape, or both size and shape too large for percutaneous or intravascular delivery, for example a size, shape, or both size and shape too large for percutaneous or intravascular delivery toward a bodily cavity, or a size, shape, or both size and shape too large for percutaneous or intravascular delivery away from a bodily cavity. In some embodiments, the fanned arrangement 370 is formed during the expanded or deployed configuration in which the transducer-based device (e.g., manipulable portion) 300 or structure 308 thereof is manipulated to have a size, shape, or both size and shape too large for delivery through a lumen of catheter sheath 312, for example, a size, shape, or both size and shape too large for delivery through a lumen of catheter sheath 312 toward a bodily cavity, or a size, shape, or both size and shape too large for delivery through a lumen of catheter sheath 312 away from a bodily cavity.

In some embodiments, the transducer-based device (e.g., manipulable portion) 300 or structure 308 thereof includes a proximal portion 308a having a first domed shape 309a and a distal portion 308b having a second domed shape 309b when the transducer-based device (e.g., manipulable portion) 300 or structure 308 thereof is in the expanded or deployed configuration. In some embodiments, the proximal and the distal portions 308a, 308b include respective portions of elongate members 304. In some embodiments, the transducer-based device (e.g., manipulable portion) 300 or structure 308 thereof is arranged to be delivered or advanced distal portion 308b first (e.g., distal portion 308b ahead of proximal portion 308a) into a bodily cavity when the transducer-based device (e.g., manipulable portion) 300 or structure 308 thereof is in the unexpanded or delivery configuration as shown in FIG. 2A. In some embodiments, the proximal and the distal portions 308a, 308b are arranged in a clam shell configuration in the expanded or deployed configuration shown in FIG. 2B. In various example embodiments, each of the front surfaces 318a (two called out in FIG. 2B) of the intermediate portions 309 of the plurality of elongate members 304 face outwardly from the structure 308 when the structure 308 is in the deployed configuration. In various example embodiments, each of the front surfaces 318a of the intermediate portions 309 of the plurality of elongate members 304 are positioned adjacent an interior tissue surface of a bodily cavity in which the structure 308 (i.e., in the deployed configuration) is located. In various example embodiments, each of the back surfaces 318b (two called out in FIG. 2B) of the intermediate portions 309 of the plurality of elongate members 304 face an inward direction when the structure 308 is in the deployed configuration.

The transducers 306 may be arranged in various distributions or arrangements in various embodiments. In some embodiments, various ones of the transducers 306 are spaced apart from one another in a spaced-apart distribution in the delivery configuration shown in FIG. 2A. In some embodiments, various ones of the transducers 306 are arranged in a spaced-apart distribution in the deployed configuration shown in FIG. 2B. In some embodiments, various pairs of transducers 306 are spaced apart with respect to one another. In some embodiments, various regions of space are located between various pairs of the transducers 306. For example, in FIG. 2B the transducer-based device 300 includes at least a first transducer 306a, a second transducer 306b, and a third transducer 306c (all collectively referred to as transducers 306). In some embodiments each of the first, the second, and the third transducers 306a, 306b, and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device 300 (i.e., a portion of an elongate member 304) is between the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter device. For example, an elongated catheter member may be used to distribute the transducers in a linear or curvilinear array. Basket catheters or balloon catheters may be used to distribute the transducers in a two-dimensional or three-dimensional array.

In some embodiments, a manipulable portion, such as, but not limited to, a transducer-based device (e.g., 200, 300, 400, or 502) is manipulated to transition between an unexpanded or delivery configuration (e.g., FIG. 2A) and an expanded or deployed configuration (e.g., FIG. 2B) manually (e.g., by a user's manual operation) or at least in part by way of motor-based driving (e.g., from the energy source device system 340) of one or more actuators. Motor-based driving may augment or otherwise be in response to manual actions, may be responsive to automated control of a data processing device system (e.g., 310 in FIGS. 2A and 2B), or may use a hybrid manual-automated approach.

In this regard, FIG. 4 show some or all of a catheter system 500, which includes a manipulable portion 502, according to various embodiments. In this regard, it should be noted that any of the catheter systems described herein may also be referred to as a medical system or medical device system and, consequently, that catheter or catheter device system 500 may be referred to as a medical or medical device system 500. In some embodiments, the manipulable portion 502 corresponds to the transducer-based device 200 or 300, although the manipulable portion 502 need not be a transducer-based device and may be some other form of catheter-based manipulable portion (e.g., a stent or other implant). In this regard, the systems of FIG. 4 (as well as the other remaining figures) may be particular implementations of the systems of FIGS. 1 and 2, according to some embodiments. Accordingly, descriptions herein regarding the systems of FIGS. 1 and 2 apply to the systems of FIG. 4 (as well as the other remaining figures), according to some embodiments.

Figure 4A:
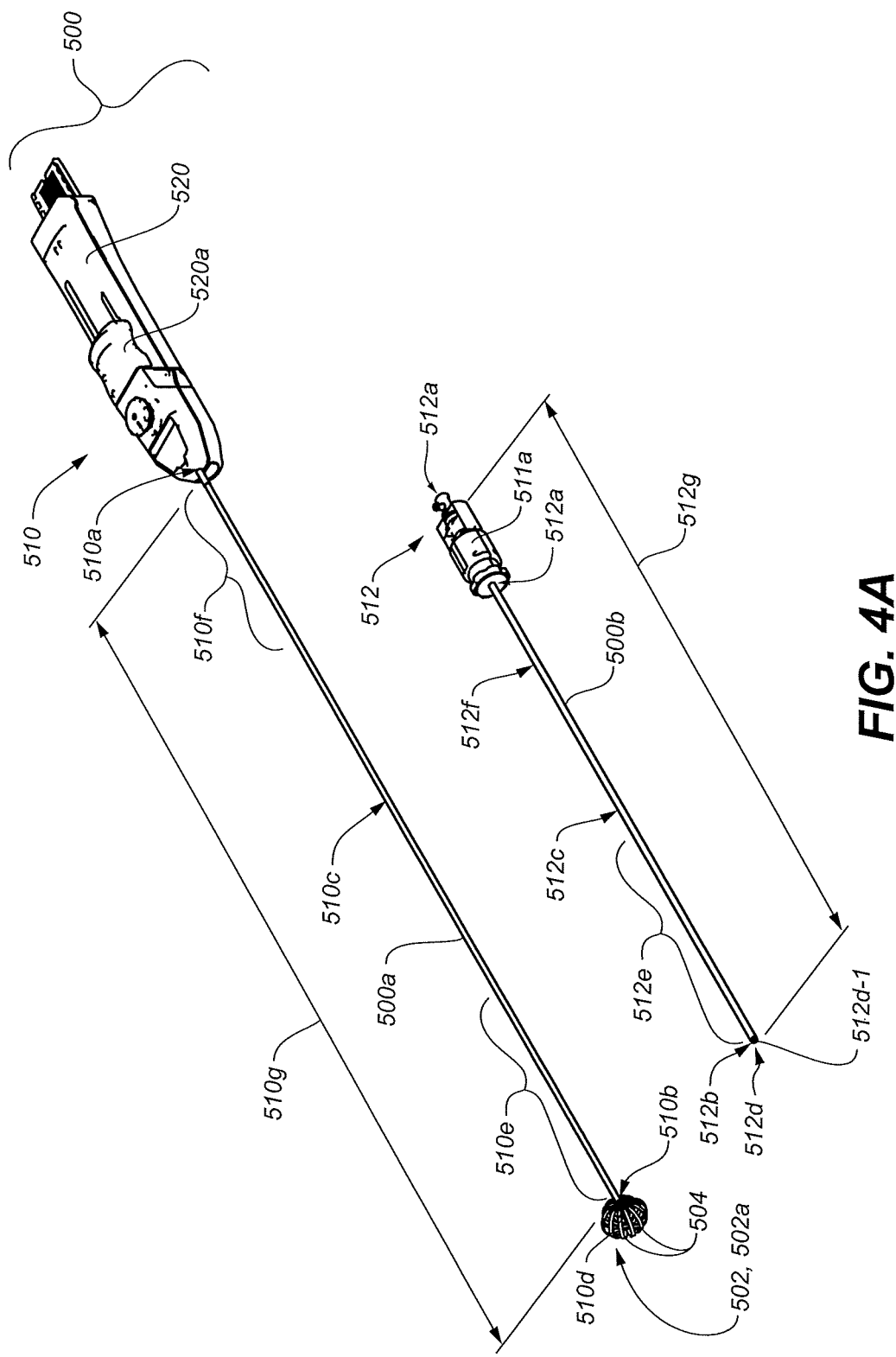
FIG. 4A is a perspective representation of a catheter system, according to some example embodiments.

As shown in FIG. 4A, catheter system 500 includes various devices including a catheter 510, which includes a catheter shaft member 500a (also referred to as elongate shaft member 500a) (e.g., the same or similar to catheter body 314) according to various embodiments. In some embodiments, catheter system 500 (which may also be referred to as a catheter) includes a catheter sheath member 500b (also referred to as elongate shaft member 500b).

Elongate shaft member 500a includes proximal end portion 510f that includes a proximal end 510a of the elongate shaft member 500a; a distal end portion 510e that includes a distal end 510b of the elongate shaft member 500a; and an intermediate or elongated portion 510c extending between the proximal end 510a and the distal end 510b (e.g., extending along the elongate shaft member 510a along a path that connects proximal end 510a and distal end 510b). In some embodiments, the distal end 510b is arranged to be deliverable ahead of the proximal end 510a through a bodily opening leading to a bodily cavity. In various embodiments, elongate shaft member 500a includes one or more lumens, each of at least some of the one or more lumens extending between proximal end 510a and distal end 510b (e.g., extending along the elongate shaft member 510a along a path that connects proximal end 510a and distal end 510b). In various embodiments associated with various ones of FIGS. 4, elongate shaft member 500a includes a first lumen 510d extending between (or connecting, in some embodiments) proximal end 510a and distal end 510b. In some embodiments, the first lumen 510d includes a first end located at or proximate the proximal end 510a and a second end located at or proximate the distal end 510b. The second end of the first lumen 510d may be included in the distal end portion 510e of the elongate shaft member 500a. In some embodiments associated with various ones of FIGS. 4, the manipulable portion 502 is connected to the distal end portion 510e of the elongate shaft member 500a at a location at or proximate the distal end 510b. In some embodiments, the manipulable portion 502 is physically coupled or otherwise coupled to the distal end portion 510e. In various embodiments, each of the proximal end portion 510f and the distal end portion 510e includes a respective exterior surface or surface portion (e.g., a circumferential or cylindrical exterior surface or surface portion) of the elongate shaft member 500a.

Elongate shaft member 500b forms part of a catheter sheath 512 (e.g., the same or similar to sheath 312) and includes a proximal end portion 512f that includes a proximal end 512a of the elongate shaft member 500b; a distal end portion 512e that includes a distal end 512b of the elongate shaft member 500b; and an intermediate or body portion 512c between the proximal end 512a and the distal end 512b. It is noted that FIG. 4A shows two instances of the proximal end 512a, as such proximal end 512a may be considered to be in either location or at a location within a coupling assembly 511a, depending upon the embodiment. In some embodiments, the distal end 512b is arranged to be deliverable ahead of the proximal end 512a through a bodily opening leading to a bodily cavity. In various embodiments, elongate shaft member 500b includes one or more lumens, each of at least some of the one or more lumens extending between proximal end 512a and distal end 512b (e.g., extending along the elongate shaft member 500b along a path that connects proximal end 512a and distal end 512b). In various embodiments associated with various ones of FIGS. 4, elongate shaft member 500b includes a first lumen 512d extending between (or connecting, in some embodiments) proximal end 512a and distal end 512b. In some embodiments, the first lumen 512d includes a first end located at or proximate the proximal end 512a and a second end located at or proximate the distal end 512b. The second end of the first lumen 512d may be included in the distal end portion 512e of the elongate shaft member 500b. In various embodiments, each of the proximal end portion 512f and the distal end portion 512e includes a respective exterior surface or surface portion (e.g., a circumferential or cylindrical exterior surface or surface portion) of the elongate shaft member 500b.

In various embodiments, elongate shaft member 500b provides a passageway for at least a portion of elongate shaft member 500a to be delivered therethrough to a location within a body during a medical procedure. In some embodiments, elongate shaft member 500b is deployed percutaneously or intravascularly into a body. In various embodiments, at least a portion of elongate shaft member 500b (e.g., at least a portion of the catheter sheath 512) is delivered distal end 512b first (e.g., ahead of the proximal end 512a) through a naturally occurring bodily opening toward a bodily cavity. For instance, the catheter sheath 512 may be receivable in, insertable into, or positionable in a bodily opening. In some embodiments, the bodily opening is accessed by a natural orifice or port provided by the body. In some embodiments, the bodily opening is accessed by a perforation made in bodily tissue. In various embodiments, a portion or part of elongate shaft member 500a (e.g., at least part of the catheter 510) is received in, receivable in, or sized for delivery through the first lumen 512d of the elongate shaft member 500b to a bodily cavity or to deliver the manipulable portion 502 through the first lumen 512d of the elongate shaft member 500b to a bodily cavity (e.g., a bodily vessel, chamber or cavity within a bodily organ). In this regard, in some embodiments, at least part of the elongate shaft member 500a including the distal end 510b is sized for delivery through a bodily opening leading to a bodily cavity located in a body.

It is understood that, although each of elongate shaft member 500a and elongate shaft member 500b is depicted in FIG. 4A in an essentially straight configuration, each of elongate shaft member 500a (or at least part of the elongate shaft member 500a receivable in the lumen 512d of the elongate shaft member 500b) and elongate shaft member 500b may be flexible or bendable or may include one or more flexible or bendable portions that allow bending or deflection or the assumption of a bent or curved (e.g., arcuate) form, e.g., during or for delivery to a bodily cavity. It is further understood that each of elongate shaft member 500a and elongate shaft member 500b may include a respective longitudinal axis extending between the respective ones of proximal ends 510a, 512a and respective ones of distal ends 510b, 512b. As each of the elongate shaft members 500a, 500b may, according to various embodiments, assume a bent or arcuate form, their respective longitudinal axes may also assume a corresponding bent or arcuate form.

In various embodiments, elongate shaft member 500a is arranged with respect to elongate shaft member 500b such that the distal end 510b of elongate shaft member 500a is configured, arranged, or sized to be delivered through the first lumen 512d of elongate shaft member 500b prior to at least the elongated portion 510c of the elongate shaft member 500a, when the distal end 510b of the elongate shaft member 500a is delivered toward or to the bodily cavity. In various embodiments, elongate shaft member 500a of catheter 510 is arranged with respect to the elongate shaft member 500b of catheter sheath 512 such that the distal end 510b of shaft 500a is configured, arranged, or sized to be delivered through the first lumen 512d of the elongate shaft member 500b in a direction extending from the proximal end 512a of elongate shaft member 500b toward the distal end 512b of elongate shaft member 500b when the distal end 510b of elongate shaft member 500a is delivered toward or to the bodily cavity.

Figure 4B:
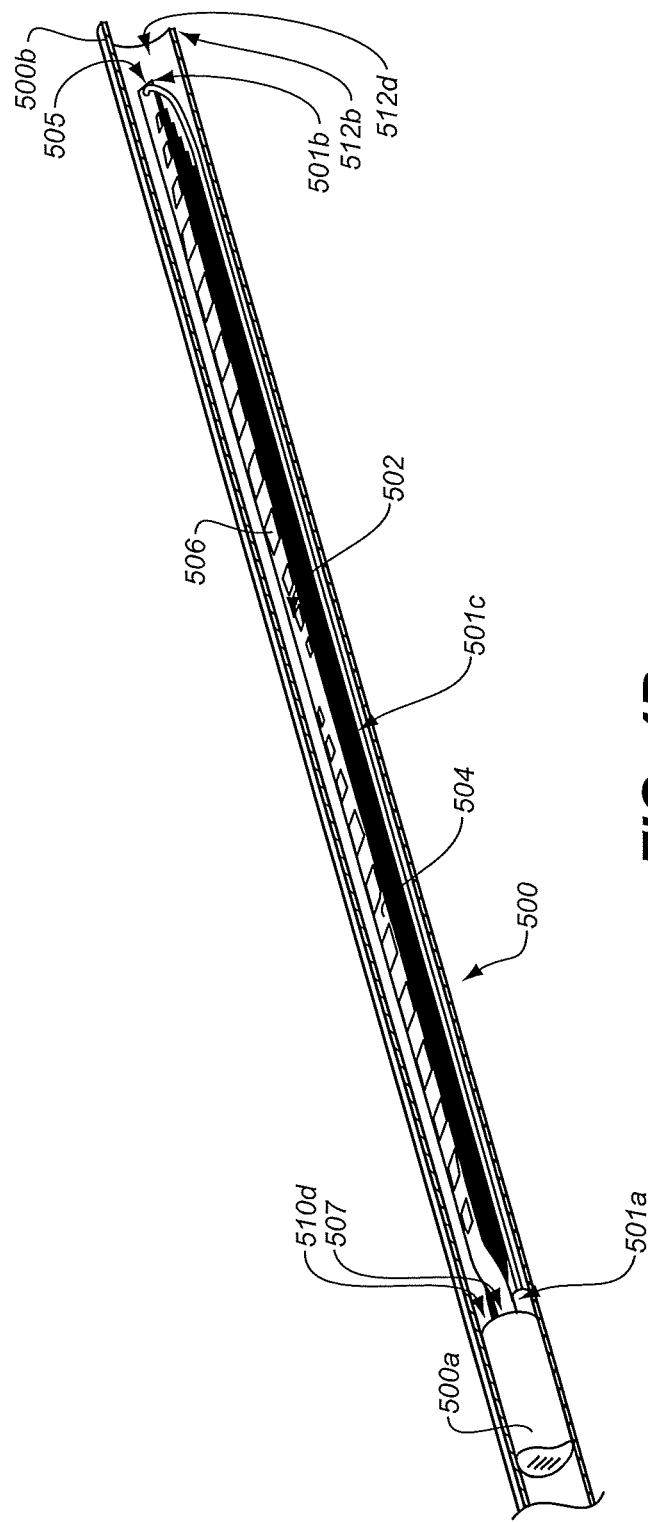
FIG. 4B is a perspective representation of a portion of the catheter system of FIG. 4A, according to some example embodiments.

In various embodiments, the manipulable portion 502 includes a proximal end portion 501a (e.g., in the vicinity of elongate member proximal ends 507 in FIG. 4B), a distal end portion 501b (e.g., in the vicinity of elongate member distal ends 505 in FIG. 4B), and an elongated portion 501c (e.g., FIG. 4B) extending between the proximal end portion 501a and the distal end portion 501b of the manipulable portion 502. In some embodiments, the manipulable portion 502 is delivered and advanced outwardly, (e.g., distal end portion 501b first with respect to or as compared to other parts of the manipulable portion 502), through the first lumen 512d of the elongate shaft member 500b of catheter sheath 512 toward or to the bodily cavity as the elongate shaft member 500a is advanced accordingly through first lumen 512d.

It is noted that each of elongate shaft member 500a and elongate shaft member 500b has a respective elongated portion that can have longitudinal or axial components. For example, the elongate shaft member 500a has a longitudinal length 510g from the proximal end 510a to the distal end 510b, according to some embodiments. In some embodiments, the longitudinal length 510g is sufficient to position the proximal end 510a outside a body including a bodily cavity during a state in which the distal end 510b (or the manipulable portion 502) is positioned in the bodily cavity. Similarly, the elongate shaft member 500b has a longitudinal length 512g from the proximal end 512a to the distal end 512b, according to some embodiments. In some embodiments, the longitudinal length 512g is sufficient to position the proximal end 512a outside a body including a bodily cavity during a state in which the distal end 512b (or the manipulable portion 502) is positioned in the bodily cavity. As used in this disclosure, words such as "longitudinal" or "axial" are not limited to various members having generally straight forms but may include members that have bent or arcuate forms or forms that have been bent from a generally straight form into a generally non-straight form.

In various embodiments, manipulable portion 502 is selectively configurable or moveable, e.g., based at least upon user (e.g., a health care provider, technician, or other user) input (e.g., by way of various actuators provided in or on housing 520 of catheter, such as actuator 520a discussed below). For example, in some embodiments, the manipulable portion 502 may form at least part of a steerable portion of elongate shaft member 500a. Catheter devices employing steerable portions may be used to better negotiate tortuous paths sometimes encountered during delivery to a bodily cavity. Catheter devices employing steerable portions may be employed to better achieve a desired positioning of various devices (e.g., implants or transducer systems). In some embodiments, the manipulable portion 502 may be selectively detachable from the elongate shaft member 500a. For example, the manipulable portion 502 may, in some embodiments, form part of an implant (e.g., a stent). In some of these embodiments, an implant provided at least in part by the manipulable portion 502 may be selectively configurable or moveable (e.g., by way of a modulation or other actuator described in this disclosure) between a delivery configuration in which the implant is appropriately sized for delivery through the first lumen 512*d* toward or to a particular location in the bodily opening or bodily cavity and a deployed configuration in which the implant is sized too large for delivery through the first lumen 512*d* toward or to the particular location in the bodily opening or bodily cavity. In some of these embodiments, the implant may be positioned in the deployed configuration when implanted or otherwise brought into engagement with tissue (e.g., a stent that is selectively expanded to grip or to otherwise be secured within a bodily vessel).

In some embodiments associated with various ones of FIGS. 4, manipulable portion 502 forms a part of a transducer-based device (e.g., 200, 300) with various sets of one or more transducers located on, or forming part of the manipulable portion 502. For example, in some embodiments, manipulable portion 502 includes a structure 502*a* (e.g., the same or similar to structure or frame 308) and various transducers 506 (only one called out in FIG. 4B, and which may be the same or similar to transducers 220, 306, 406) that are located on or carried by the manipulable portion 502 or the structure 502*a* thereof. In a manner that is the same or similar to other embodiments described above in this disclosure, manipulable portion 502 or structure 502*a* is selectively configurable or moveable (e.g., by way of a modulation or other actuator described in this disclosure) between an unexpanded or delivery configuration in which at least the manipulable portion 502 or structure 502*a* is appropriately sized, shaped, or both sized and shaped for delivery through the first lumen 512*d* of the elongate shaft member 500*b* of catheter sheath 512 at least toward or to a bodily cavity located in a body and an expanded or deployed configuration in which at least the structure 502*a* is sized, shaped, or both sized and shaped too large for delivery through the first lumen 512*d* of the catheter sheath 512 at least toward or to the bodily cavity. In some embodiments, a size, shape, or both size and shape of the manipulable portion 502 or structure 502*a* in the expanded or deployed configuration is or are larger than a corresponding size, shape, or both size and shape of the manipulable portion 502 or structure 502*a* in the unexpanded or delivery configuration. In some embodiments, in the unexpanded or delivery configuration, the manipulable portion 502 or structure 502*a* is sized to permit delivery of the manipulable portion 502 or structure 502*a* through a bodily opening leading to the bodily cavity, and in the deployed or expanded configuration, the manipulable portion 502 or structure 502*a* is sized too large to permit delivery of the manipulable portion 502 or structure 502*a* through the bodily opening leading to the bodily cavity.

In various embodiments, the manipulable portion 502 or structure 502*a* thereof is physically coupled or otherwise coupled to the elongate shaft member 500*a* at a location at least proximate the distal end 510*b* of the elongate shaft member 500*a*. In this regard, the manipulable portion 502 or structure 502*a* thereof may include a plurality of elongate members 504 (two called out in FIG. 4A), such as elongate members 304, that are physically coupled to elongate shaft member 500*a*, which is employed to transport the elongate members 504 through first lumen 512*d* when the structure 502*a* is in an unexpanded or delivery configuration. The number of elongate members 504 shown in various ones of FIG. 4 is non-limiting.

Reference will now be made to FIGS. 5, which illustrate, among other things, the flushing of the elongate shaft member 500*b* of the catheter sheath 512, according to some embodiments. FIGS. 6, discussed further below, illustrate, among other things, the flushing of the elongate shaft member 500*a* of the catheter 510, according to some embodiments. In some embodiments, the elongate shaft member 500*a* and the elongate shaft member 500*b* are flushed at different times.

Figure 5A:
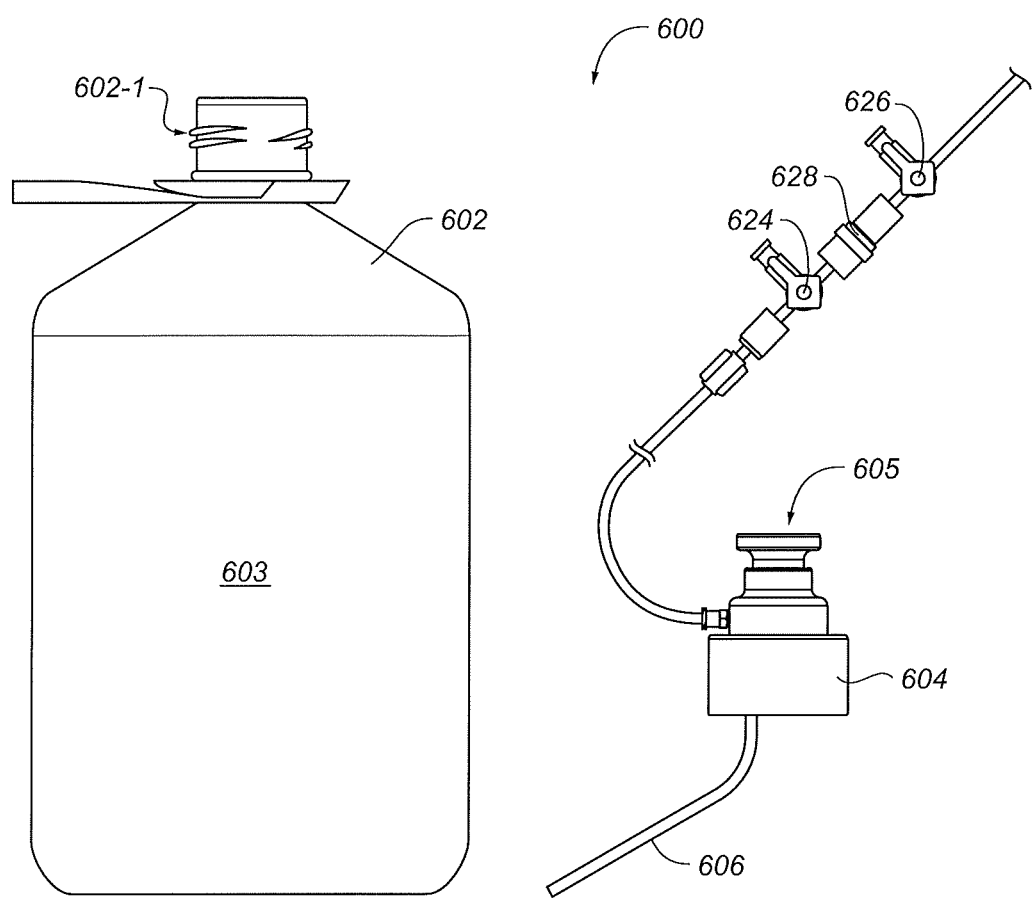
FIG. 5A illustrates a flushing kit including a cap, according to some example embodiments.

FIG. 5A illustrates at least a portion of a flushing kit 600 employed to flush a catheter according to various embodiments. The catheter may include an elongate shaft member that includes a proximal end, a distal end and a length from the proximal end to the distal end. In this regard, the catheter may be catheter 510. Also in this regard, the elongate shaft member may form part of a catheter sheath, such as catheter sheath 312 or catheter sheath 512 (e.g., elongate shaft member 500*b* including proximal end 512*a* and distal end 512*b*). For ease of discussion, and according to some embodiments in which flushing kit 600 is employed with a catheter sheath, reference will be made to elongate shaft member 500*b* although it is understood that other catheter sheaths may be readily employed. As per another example, the elongate shaft member may form part of a catheter, such as catheter 206, the catheter system of FIG. 3 (e.g., elongate shaft member 314), or catheter 510 (e.g., elongate shaft member 500*b* including proximal end 510*a* and distal end 510*b*). For ease of discussion, and according to some embodiments in which flushing kit 600 is employed with a catheter, reference will be made to elongate shaft member 500*a*, although it is understood that other catheters may be readily employed.

In various embodiments, as discussed above, the elongate shaft member 500*a* includes a first lumen 510*d*. The first lumen 510*d* may include a first end at least proximate the proximal end 510*a* of the elongate shaft member 500*a* and may include a second end at least proximate the distal end 510*b* of the elongate shaft member 500*a*. Similarly, the elongate shaft member 500*b* of catheter sheath 512 may include a first lumen 512*d* including a first end located at least proximate the proximal end 512*a* and may include a second end located at least proximate the distal end 512*b* of elongate shaft member 500*b*. In this regard, various lumens may be provided in elongate shaft member 500*a*, elongate shaft member 500*b*, or both, to provide a passageway for various control leads (e.g., control leads 317) that may extend therethrough to various elongate members 304 or transducers 306 thereof that may form part of manipulable portion 502. Various lumens may be additionally or alternatively provided in elongate shaft member 500*a*, elongate shaft member 500*b*, or both, to provide a passageway for various control lines that may couple an actuator system (e.g., an actuator system provided in or on housing 520) to the manipulable portion 502 to selectively manipulate the manipulable portion 502 (e.g., selectively manipulating the manipulable portion 502 between an unexpanded or delivery configuration and an expanded or deployed configuration). In various embodiments, the distal end (e.g., 510*b*, 512*b*) of the elongate shaft member is arranged to be deliverable ahead of the proximal end (e.g., 510*a*, 512*a*) of the elongate shaft member through a bodily opening leading to a bodily cavity or a bodily organ. In some embodiments, the manipulable portion 502 is located at the distal end 510*b* of the elongate shaft member 500*a* or is located closer to the distal end 510*b* of the elongate shaft member 500*a* than it is to the proximal end 510*a* of the elongate shaft member 500*a*. In some embodiments, the manipulable portion 502 is not located between the distal end 510*b* of the elongate shaft member 500*a* and the proximal end 510*a* of the elongate shaft member 500*a*. In some embodiments, the housing 520 is located at the proximal end 510*a* of the elongate shaft member 500*a* or is located closer to the proximal end 510*a* of the elongate shaft member 500*a* than it is to the distal end 510*b* of the elongate shaft member 500*a*. In some embodiments, the housing 520 is not located between the distal end 510*b* of the elongate shaft member 500*a* and the proximal end 510*a* of the elongate shaft member 500*a*. In some embodiments, the length (e.g., longitudinal length 510*g*, 512*g*) of the elongate shaft member is sufficient to position the proximal end (e.g., 510*a*, 512*a*) of the elongate shaft member outside a body that includes the bodily cavity during a state in which the distal end (e.g., 510*b*, 512*b*) of the elongate shaft member is positioned in the bodily cavity.

Figure 5B:
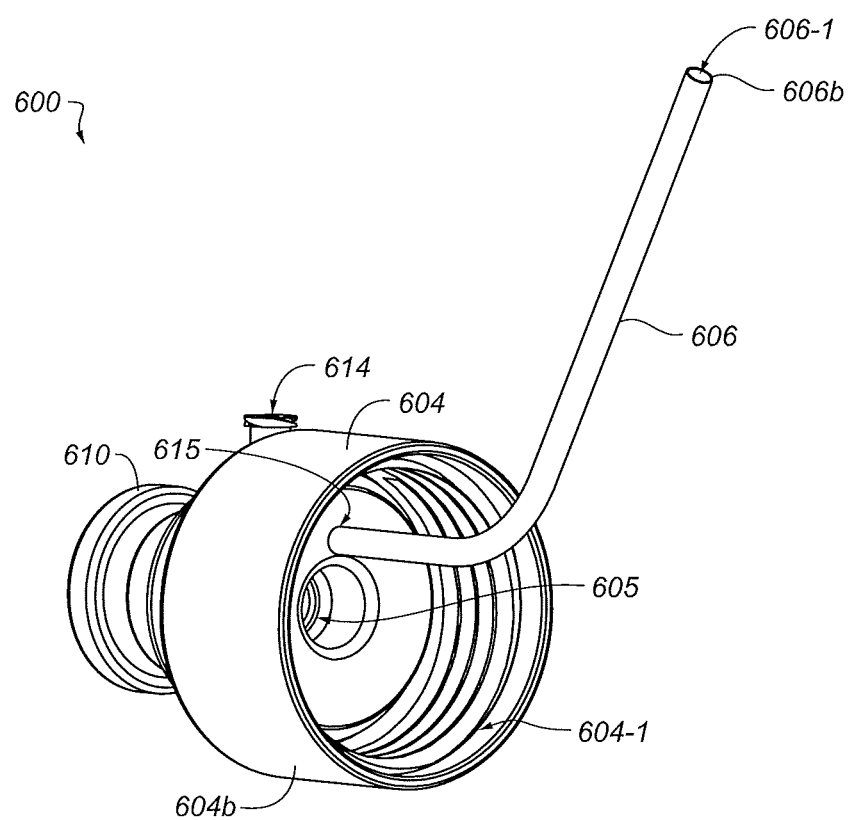
FIG. 5B is a perspective representation of the cap of FIG. 5A, according to some example embodiments.
Figure 5C:
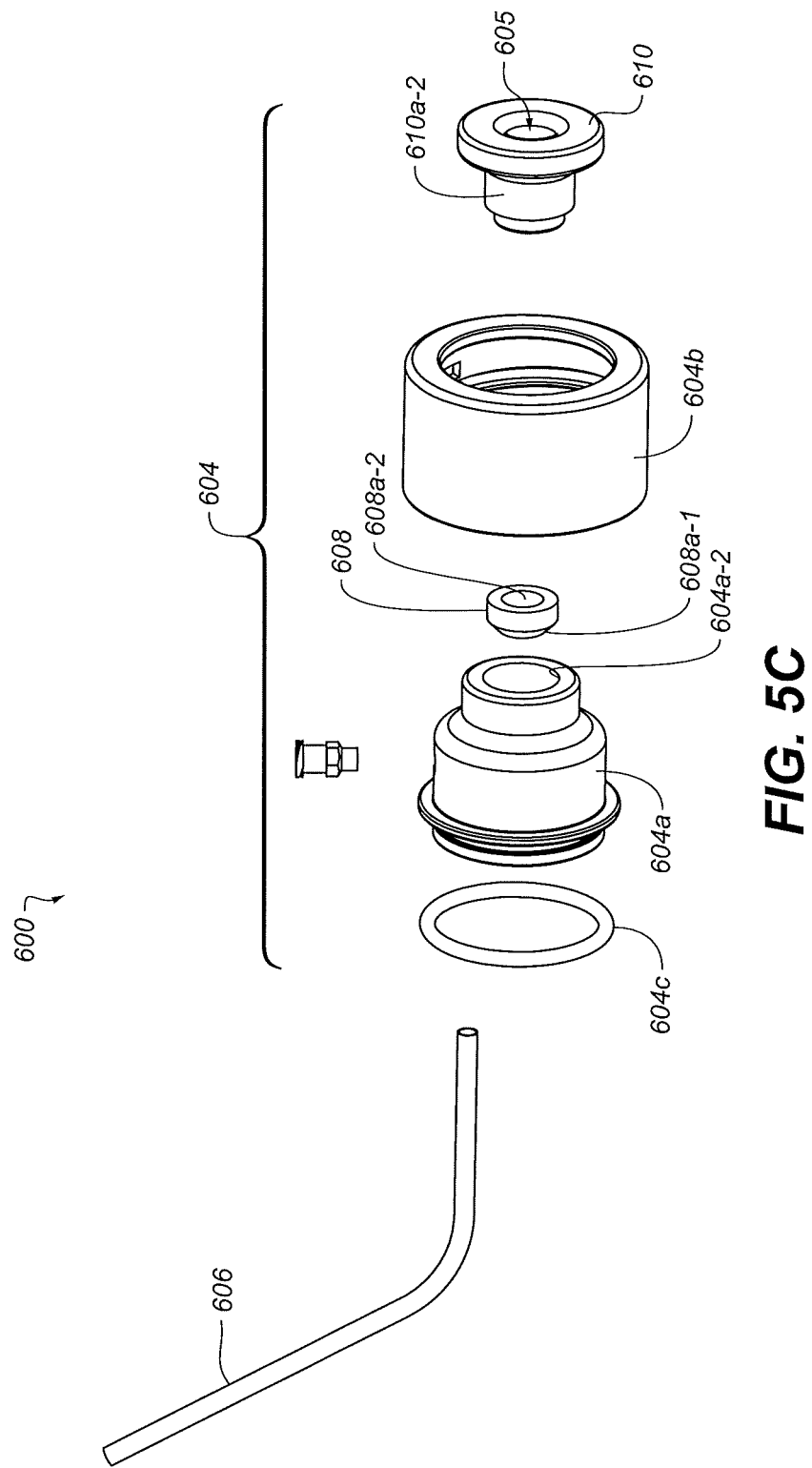
FIG. 5C is an exploded view of the cap of FIG. 5B, according to some example embodiments.

According to various embodiments, flushing kit 600 may include a vessel 602 that includes an interior cavity 603 and a first port 605 in fluid communication with the interior cavity 603. In some embodiments, the first port 605 is considered to be not part of the vessel 602. In some embodiments, the vessel 602 includes a removable cap 604, the cap 604 removable to provide access interior cavity 603. FIG. 5B is a perspective view of at least cap 604 according to various embodiments. FIG. 5C is an exploded perspective view of at least cap 604. In some embodiments, cap 604 may be completely removable (e.g., completely separable) from vessel 602 to permit or allow greater access to interior cavity 603. In some embodiments, cap 604 may be partially removable while still being physically coupled (e.g., by a hinge or other connector) to vessel 602. In some embodiments associated with FIGS. 5, cap 604 includes a first screw thread portion 604-1 (e.g., an internal screw thread) that is threadedly couplable to a second screw thread portion 602-1 provided on vessel 602. A seal 604*c* (e.g., a seal made from an elastomeric material, such as silicone or neoprene) may be employed according to various embodiments to seal cap 604 to vessel 602.

The use of cap 604 may be motivated for various reasons. For example, cap 604 may be provided to allow a relatively larger access port to the interior cavity 603 of the vessel 602 than any other port that may be provided on the vessel 602. A relatively larger access port may be advantageous to allow a required quantity of a liquid or other fluid to be transferred to the interior cavity 603 in a timely or expeditious manner, according to some embodiments. A relatively larger access port may be advantageous to allow other elements of the flushing kit 600 (e.g., conduit member 606, described below) whose size, shape, or both size and shape would make it difficult to insert or otherwise position into interior cavity 603 via a port of a relatively smaller size.

In some embodiments, the first port 605 is sized to removably receive at least part of the distal end portion (e.g., 510*e* or 512*e*, depending on which elongate shaft member 500*a* or 500*b* is being flushed) of the elongate shaft member (500*a* or 500*b*) to be flushed. In some embodiments, the phrase "removably receive" in this and similar contexts means that the port 605 is sized to receive the distal end portion of the elongate shaft member in a manner that does not permanently couple the port 605 and the distal end portion of the elongate shaft member. For example, any coupling that may exist between the elongate shaft member 500*a* or 500*b* and the vessel 602 once the distal end portion (e.g., 510*e* or 512*e*, depending on which elongate shaft member 500*a* or 500*b* is being employed) of the elongate shaft member (500*a* or 500*b*) is received (e.g., inserted) in the first port 605 may be manipulated (for example, without the use of a tool or tools) to readily allow removal of the distal end portion from the first port 605. In various embodiments, the at least part of the distal end portion (e.g., 510*e*, 512*e*) includes both the distal end (e.g., 510*b*, 512*b*) of the elongate shaft member and a second end or distal end of the first lumen extending through the elongate shaft member. For example, in FIG. 4A, the distal end portion 512*e* of the elongate shaft member 500*b* includes the distal end 512*b* of the elongate shaft member 500*b* and the distal or second end 512*d*-1 of the first lumen 512*d* of the elongate shaft member 500*b*.

In various embodiments, the first port 605 is sized to permit delivery of the manipulable portion 502 or structure 502*a* through the first port 605 when the manipulable portion 502 or structure 502*a* is in the unexpanded or delivery configuration. In some embodiments, the first port 605 is sized to restrict delivery of the manipulable portion 502 or structure 502*a* through the first port 605 when the manipulable portion 502 or structure 502*a* is in the expanded or deployed configuration.

In various embodiments, vessel 602 is configured to not be deliverable, or configured to be incapable of being deliverable, through the same bodily opening (e.g., via a percutaneous or intravascular delivery) that the elongate shaft member (500*a*, 500*b*) is configured for delivery through. For example, the vessel 602 may include a size (e.g., an overall size or dimension) that is too large or renders the vessel 602 too large for delivery of the vessel 602 through the bodily opening leading to a bodily cavity to which the elongate shaft member (500*a*, 500*b*) is to be delivered. For example, in various ones of the FIGS. 5, vessel 602 is sized much larger than a size of first port 605, which is sized according to various embodiments to allow for a sliding fit with the at least part of the distal end portion (e.g., 510*e*, 512*e*) of the elongate shaft member (e.g., 500*a*, 500*b*). Accordingly, the size of the first port 605 may approximate the size (e.g., at least be smaller than the size) of the bodily opening through which the elongate shaft member (500*a*, 500*b*) is to be delivered. Consequently, the vessel 602 may be physically incapable of being delivered through such bodily opening because its size is much larger than that of the first port 605.

In some embodiments, vessel 602 may be incapable of being deliverable through the bodily opening in various states. For example, in some embodiments, the vessel 602 may include a size (e.g., an overall size or dimension) that is too large or renders the vessel 602 too large for delivery of the vessel 602 through the bodily opening leading to a bodily cavity to which the elongate shaft member (500*a*, 500*b*) is to be delivered at least in a state in which a particular portion or the entirety of the interior cavity 603 is void of a particular liquid (for example, a liquid as described below in this disclosure, such as a flushing liquid, e.g., saline). In some embodiments, the vessel 602 may include a size (e.g., an overall size or dimension) that is too large or renders the vessel 602 too large for delivery of the vessel 602 through the bodily opening at least in a state in which a particular portion or the entirety of the interior cavity 603 is void of any particular liquid (e.g., void of any liquid whatsoever). In some embodiments, the vessel 602 may include a size (e.g., an overall size or dimension) that is too large or renders the vessel 602 too large for delivery of the vessel 602 through the bodily opening at least in a state in which a portion of the interior cavity 603 in filled with a particular liquid and another portion of the interior cavity 603 is not filled with the particular liquid. Similarly, in some embodiments, the vessel 602 may include a size (e.g., an overall size or dimension) that is too large or renders the vessel 602 too large to fit in the bodily cavity to which the elongate shaft member (500*a*, 500*b*) is to be delivered at least in each of one or more or all of the above-described states. For example, the vessel 602 may have the above-described size(s) at least in embodiments where the vessel 602 is formed of a rigid or substantially rigid structure that may be incapable of fitting into the bodily cavity or delivery though the bodily opening leading to the bodily cavity regardless of whether it is empty of liquid or filled at least in part with liquid. FIG. 5A illustrates the vessel 602 having such a rigid or substantially rigid structure. According to some embodiments, the vessel 602 illustrated in FIG. 5A is sufficiently rigid to not collapse at least throughout execution of the methods described herein, while allowing the walls of such vessel 602 to slightly expand outward or compress inward depending upon the state of pressurization of the liquid therein, as described herein. In some embodiments, the vessel 602 may include a structure that is incapable of collapsing to a size suitable for delivery through the bodily opening leading to the bodily cavity. For example, the vessel 602 may include a flexible structure that is collapsible or compressible to a minimum size that is incapable of allowing delivery of the vessel 602 through the bodily opening leading to the bodily cavity.

Even if the vessel 602 is a flexible or substantially compliant structure that may allow sufficient compression to possibly fit through the bodily opening, the mere presence of the vessel 602 during the delivery of the elongate shaft member (e.g., 500*a*, 500*b*) through the bodily opening may impede, restrict, or prevent a required functioning of the elongate shaft member or catheter that comprises the elongate shaft member. For example, if the elongate shaft member is part of a catheter sheath (e.g., elongate shaft member 500*b*), a delivery of an assembly including the elongate shaft member and vessel 602 (i.e., positioned over the distal end portion (e.g., 512*e*) of the elongate shaft member) through the bodily opening would likely position the vessel 602 so as to impede a subsequent delivery of the catheter or other medical instrument through a lumen of the elongate shaft member. If the elongate shaft member is part of a catheter (e.g., elongate shaft member 500*a*), a delivery of an assembly including the elongate shaft member and vessel 602 (i.e., positioned over the distal end portion (e.g., 510*e*) of the elongate shaft member) through the bodily opening would likely position the vessel 602 so as to impede a subsequent operation of manipulable portion 502 with respect to tissue within the bodily cavity (e.g., tissue ablation or the sensing of various physiological parameters such as tissue electrical potential). In this regard, when the flushing kit 600 is employed, the at least part of the distal end portion (e.g., 510*e*, 512*e*) of the elongate shaft member (e.g., 500*a*, 500*b*) inserted into the vessel 602 is removed from the interior cavity 603 prior to a delivery of at least the distal end portion (e.g., 510*e*, 512*e*) of the elongate shaft member (e.g., 500*a*, 500*b*) through the bodily opening leading to the bodily cavity, according to some embodiments.

Referring to the exploded view of FIG. 5C, the flushing kit 600 includes, according to some embodiments, a seal or seal member 608 arranged to selectively seal an exterior surface of a first part of the distal end portion (e.g., 510*e*, 512*e*) of the elongate shaft member (e.g., 500*a*, 500*b*) to a portion of the vessel 602 at least in a state in which at least a second part of the distal end portion (e.g., 510*e*, 512*e*) of the elongate shaft member (e.g., 500*a*, 500*b*) is positioned, via the first port 605, in the interior cavity 603 at a particular location in the interior cavity 603. In some embodiments, the portion of the vessel 602, which is sealed to the exterior surface of the first part of the distal end portion of the elongate shaft member, is a portion of cap 604. In some embodiments, the portion of the vessel 602, which is sealed to the exterior surface of the first part of the distal end portion of the elongate shaft member, is a portion or surface (e.g., at least a radially-inward-facing cylindrical or circumferential engagement surface, according to some embodiments) of the seal 608 contacting or engaging the exterior surface of a part of the distal end portion 510*e* or 512*e*, whichever is being flushed. However, in some embodiments, the seal 608 is considered to be its own separate device or device system and is not considered part of the vessel 602. In some embodiments, the seal 608 is considered to be its own separate device or device system and is not considered part of the cap 604. Regardless, in various embodiments, the seal 608 may be configured to establish a seal between the seal 608 and the first part of the distal end portion (e.g., 510*e*, 512*e*) of the elongate shaft member (e.g., 500*a*, 500*b*) and to further establish (e.g., concurrently) a seal between the seal 608 and the portion of the vessel 602. In this regard, it is understood that the first part of the distal end portion (e.g., 510*e*, 512*e*) of the elongate shaft member (e.g., 500*a*, 500*b*) is still sealed to the portion of the vessel 602, according to some embodiments.

In some embodiments, the second part of the distal end portion of the elongate shaft member is a part inserted into the interior cavity 603 via the first port 605 provided by the vessel 602. In various embodiments, the second part of the distal end portion of the elongate shaft member that is positioned at the particular location in the interior cavity 603 includes the distal end (510*b*, 512*b*) of the elongate shaft member being flushed (e.g., 500*a* or 500*b*) and the distal or second end of the first lumen (e.g., 510*d*, 512*d*) that extends through the elongate shaft member. For example, according to various embodiments, the second part of the distal end portion 512*e* of elongate shaft member 500*b* includes the distal end 512*b* of the elongate shaft member 500*b* and the second end 512*d*-1 of the first lumen 512*d* of the elongate shaft member 500*b*. In various embodiments, the particular location in the interior cavity 603 is a location in the interior cavity 603 suitable to supply liquid contained in interior cavity 603 into the second end (e.g., 512*d*-1) of the first lumen (e.g., 512*d*, when elongate shaft member 500*b* is being flushed). In various embodiments, the particular location in the interior cavity 603 is a location in the interior cavity 603 suitable to supply liquid (e.g., saline or other flushing liquid) contained in interior cavity 603 into the second end (e.g., 512*d*-1) of the first lumen (e.g., 512*d*) to flush the first lumen (e.g., 512*d*) of fluid (e.g., an undesired fluid such as air) other than the liquid in a direction through the first lumen (e.g., 512*d*) extending from the second end (e.g., 512*d*-1) of the first lumen (e.g., 512*d*) toward or to the proximal or first end of the first lumen (e.g., 512*d*).

In various embodiments, the exterior surface of the first part of the distal end portion (e.g., 510*e*, 512*e*) of the elongate shaft member (e.g., 500*a*, 500*b*) that seal 608 engages is a circumferential exterior surface extending continuously around a longitudinal axis of the elongate shaft member (e.g., 500*a*, 500*b*, whichever is being flushed). In some embodiments, the exterior surface of the distal end portion (e.g., 510*e*, 512*e*) of the elongate shaft member (e.g., 500*a*, 500*b*) is a cylindrical surface. For example, in FIG. 5C, seal 608 is secured between a first body portion 604*a* of cap 604 and a seal engaging member 610 of cap 604, the seal engaging member, according to some embodiments, being coupled by a screw thread coupling to the first body portion 604*a*. For example, seal engaging member 610 may include a screw thread portion 610*a*-2 (e.g., an external screw-thread portion) configured to threadedly engage with a screw thread portion 604*a*-2 (e.g., an internal screw thread portion) of the first body portion 604a. In various embodiments, seal 608 is made from a compliant material (e.g., an elastomer such as silicone or neoprene). In various embodiments, seal 608 includes an engagement surface 608a-2 arranged to seal against the exterior surface of the distal end portion (e.g., 510e, 512e) of the elongate shaft member (e.g., 500a, 500b). In various embodiments, seal 608 is arranged to seal against the exterior surface of the distal end portion (e.g., 510e, 512e) of the elongate shaft member (e.g., 500a, 500b) when seal engaging member 610 is manipulated (e.g., turned or rotated) and compresses (e.g., via the screw thread engagement) seal 608 to cause engagement surface 608a-2 to seal against the exterior surface of the distal end portion (e.g., 510e, 512e) of the elongate shaft member (e.g., 500a, 500b). Due at least to the manipulation of the seal engaging member 610, it may be considered that the seal 608 selectively seals the exterior surface of the first part of the distal end portion (e.g., 510e, 512e) to a portion or part of the vessel 602. In various embodiments, seal 608 includes an inclined or tapered portion 608a-1 arranged to bear against an inclined or tapered portion 608a-1 (called out in FIG. 5D) to amplify the engagement forces between the engagement surface 608a-2 of seal 608 and the exterior surface of the distal end portion (e.g., 510e, 512e) of the elongate shaft member (e.g., 500a, 500b). It is noted that other exterior surfaces of the distal end portion (e.g., 510e, 512e) of the elongate shaft member (e.g., 500a, 500b) may be additionally or alternatively sealed by seal 608 according to various embodiments. For example, in some embodiments, a face surface of a distal end (e.g., 510b, 512b) of the elongate shaft member (e.g., 500a, 500b) may be sealed by seal 608. In some embodiments, seal 608 is arranged to hermetically seal the exterior surface of the distal end portion (e.g., 510e, 512e) of the elongate shaft member (e.g., 500a, 500b) to the vessel 602. In various embodiments, cap 604 includes a second body portion 604b that includes threaded portion 604-1 arranged for screw thread coupling with vessel 602. In various embodiments, second body portion 604b is free to rotate with respect to first body portion 604a.

Figure 8A:
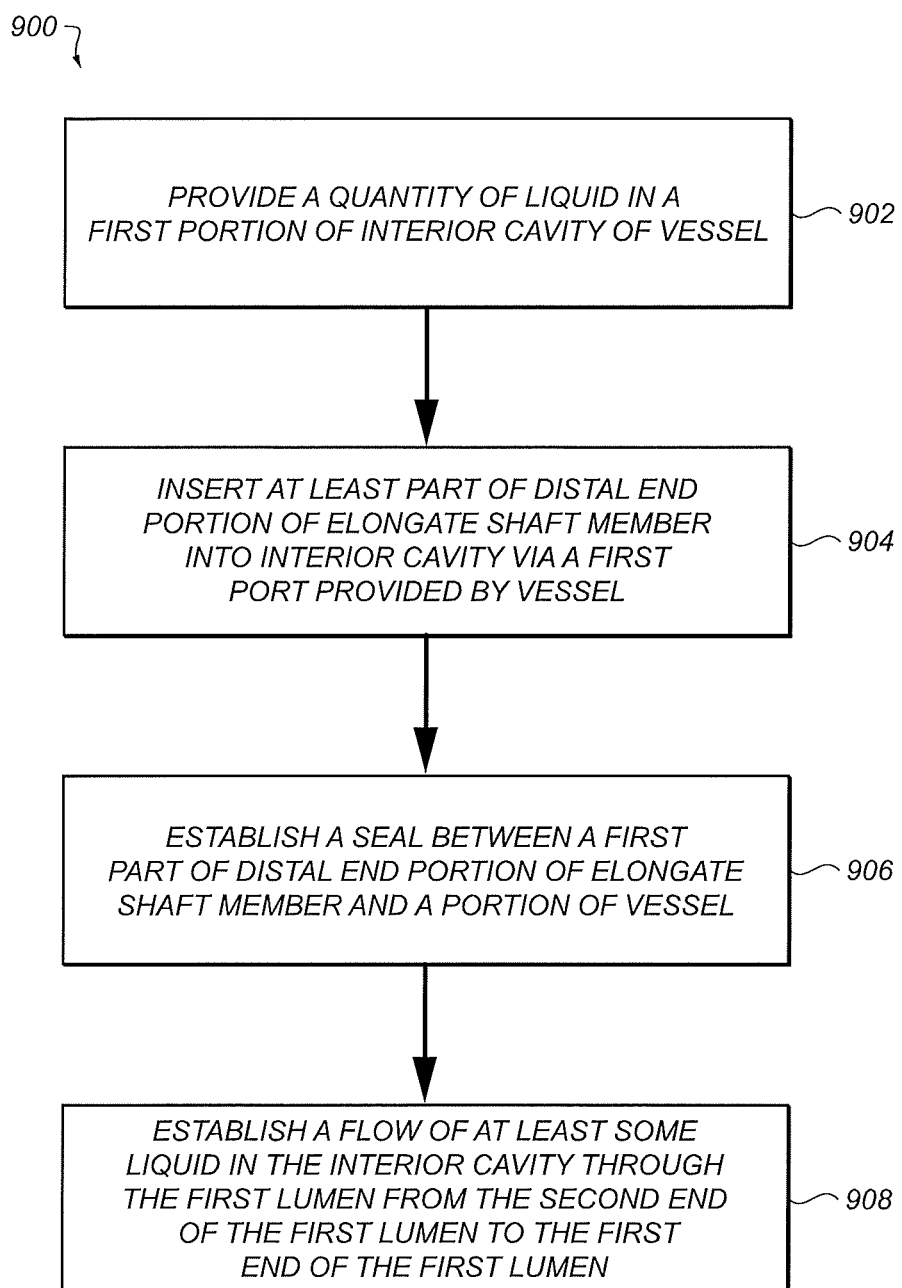
FIG. 8A is a block diagram representing a method for flushing at least a lumen of a catheter system, according to some example embodiments.

FIG. 8A is a block diagram representing a method 900 in which flushing kit 600 may be employed to establish a flow of at least some of a liquid contained in the interior cavity 603 of the vessel through the first lumen (e.g., 512d) from the distal or second end (e.g., 512d-1) of the first lumen toward, or to, a proximal or first end of the first lumen. According to some embodiments, method 900 is employed to flush a catheter that comprises an elongate shaft member (e.g., 500b) of a fluid other than the liquid in a direction from the distal end toward or to the proximal end of the first lumen. For ease of discussion, method 900 will be described with respect to catheter sheath 512 and elongate shaft member 500b. It is understood however that method 900 or variants thereof may be employed with other catheters and elongate shaft members (e.g., catheter 510 and elongate shaft member 500a).

In block 902, a quantity of liquid is provided into at least a first portion (e.g., first portion 603-1 at least in FIG. 5E) of the interior cavity 603 of vessel 602. In various embodiments, in which an undesired fluid is to be flushed from the catheter, saline may be employed as the liquid. In various cardiac procedures, heparinized saline may be employed as the liquid because of its enhanced anticoagulant properties. In various embodiments, the quantity of liquid is provided into the first portion of the interior cavity 603 in various manners. For example, in some embodiments, cap 604 is removed or otherwise manipulated to provide access to the interior cavity 603 so as to allow the liquid to be poured or otherwise delivered thereto. In some embodiments, the liquid is provided to the interior cavity 603 via an opening or port other than an opening provided access to by cap 604.

The quantity of liquid provided is sufficient to flush the first lumen 512d of a fluid other than the liquid from at least some of the first lumen 512d, in some embodiments, from the entirety of the first lumen 512d in some embodiments, and to additionally flush other components or elements of the catheter in some embodiments. In various embodiments, the quantity of liquid provided is sufficient to flush the first lumen 512d of a fluid other than the liquid from at least some of the first lumen 512d multiple times (e.g., two times or more, three times or more, etc.). In some embodiments, the quantity of liquid provided is sufficient to flush respective portions (e.g., first lumens) of each of a plurality of catheter members. For example, the quantity of liquid provided may be sufficient to fully flush at least catheter 510 and catheter sheath 512. It may be considered, in some embodiments, that the first portion 603-1 of the interior cavity 603 of the vessel 602 is sized to receive at least a quantity of liquid sufficient to flush at least the first lumen of a fluid other than the liquid.

In block 904, at least part (portion 512e-1) of distal end portion 512e of the elongate shaft member 500b is inserted into the interior cavity 603 via a first port (e.g., first port 605) provided by the vessel 602. For example, in FIG. 5E, the part 512e-1 (including the distal end 512b and the second end 512d-1 of the respective first lumen 512d) is inserted into the interior cavity 603 via a first port (e.g., first port 605) provided by the vessel 602. A first portion 603-1 of the interior cavity 603 includes a liquid 612 (e.g., saline or heparinized saline that has been provided as per block 902), according to some embodiments. According to various embodiments, vessel 602 is positioned or arranged to allow the second end 512d-1 of the first lumen 512d to be in fluid communication with the liquid 612 provided in the first portion 603-1 of the interior cavity 603, when the distal end portion 512e of the elongate shaft member 500b is inserted into the interior cavity 603 via a first port 605. For example, the distal end portion 512e may be positioned in the interior cavity 603 such that at least the second end 512d-1 of the first lumen 512d is in contact with, or is wetted by, the liquid 612 in the first portion 603-1 of the interior cavity 603. In various embodiments, the distal end portion 512e may be positioned in the interior cavity 603 to readily allow or permit a flow of the liquid 612 into the second end 512d-1 of the first lumen 512d.

In block 906, a seal is established to seal an exterior surface (e.g., a circumferential or cylindrical surface portion) of a first part (e.g., portion 512e-2) of the distal end portion 512e of the elongate shaft member 500b to at least a portion of the vessel 602. According to various embodiments, the seal may be established at least in a state in which at least a second part (e.g., portion 512e-1) of the distal end portion 512e is located (for example, via the actions of block 904) in the interior cavity 603 at a location suitable to supply the liquid 612 into the second end 512d-1 of the first lumen 512d. For example, in FIG. 5E a seal may be established by manipulating (e.g., turning or rotating) seal engaging member 610 in the appropriate direction to compress seal 608 (for example as described above in this disclosure). It is noted that other sealing mechanisms and methods may be employed in other embodiments. In some embodiments, a hermetic seal is established between the exterior surface of a first part (e.g., portion 512e-2) of the distal end portion 512e of the elongate shaft member 500b and a least a portion of the vessel 602. In some embodiments, some leakage of the liquid 612 may be tolerable. In some embodiments, the seal engaging member 610 may be manipulated (e.g., turned or rotated) to un-compress seal 608 and release the seal between the exterior surface of the first part (e.g., portion 512e-2) of the distal end portion 512e of the elongate shaft member 500b and the at least the portion of the vessel 602, for example, after the elongate shaft member 500b has been flushed.

In block 908, a flow of at least some of the liquid 612 in the first portion 603-1 of the interior cavity 603 is established through the first lumen 512d from the second end 512d-1 of the first lumen 512d toward or to a proximal or first end of the first lumen 512d. This flow of liquid 612 may be motivated for various reasons. In some embodiments, this flow of liquid 612 may be employed to flush a fluid (e.g., an undesired fluid such as air) other than the liquid 612 from the first lumen 512d.

The flow of at least some of the liquid 612 in the first portion 603-1 of the interior cavity 603 established through the first lumen 512d from the second end 512d-1 of the first lumen 512d toward or to a proximal or first end of the first lumen 512d may be accomplished or facilitated or enabled in various manners. For example, FIG. 8B includes some sub-actions employed according to block 908 to establish the required flow. In some particular embodiments, after the liquid 612 is provided in the first portion 603-1 of the interior cavity 603 and after the seal is established according to block 906, the liquid 612 in at least the first portion 603-1 of the interior cavity 603 is pressurized to levels sufficient to facilitate or enable the establishing of the required flow of liquid 612 through the first lumen 512d from the second end 512d-1 of the first lumen 512d toward or to a proximal or first end of the first lumen 512d. In this regard, at least in part, prevent fluid flow from the first lumen 512d into the interior cavity 603.

A valve 524 (FIGS. 5E, 5F), which is part of a coupling assembly 511b, and which is fluidly coupled to the first lumen 512d at a location at least proximate the proximal end 512a of elongate shaft member 500b, may be positioned to occlude the first lumen 512d during the pressurizing of the liquid 612 in the first portion 603-1 of the interior cavity 603 of the vessel 602. Note that the coupling assembly 511b, described in more detail below, may be an alternate embodiment of the coupling assembly 511a in FIG. 4A. According to some embodiments, once the liquid 612 in the first portion 603-1 of the interior cavity 603 has reached a desired pressure (e.g., approximately 0.1 atmosphere according to some embodiments), valve 524 may be manipulated to not occlude the first lumen 512d and thus allow for the required flow of liquid 612 through the first lumen 512d from the second end 512d-1 of the first lumen 512d toward or to a proximal or first end of the first lumen 512d. Unlike conventional proximal-to-distal flushing schemes that provide a flushing liquid via a branched side port that restricts the liquid flow, the ability to selectively seal the vessel to an exterior surface of the distal end portion 512e of the elongate shaft member 500b allows liquid 612 to flow directly into the second end 512d-1 of the first lumen and thus obtain flows that are not restricted and potentially avoid the greater turbulence associated with conventional branched introductions of flushing liquid. In addition to the relatively high flow rates provided by the direct entry (e.g., not via a branched path) of liquid 612 into the second end 512d-1 of the first lumen, relatively large pressures may be imparted to the liquid 612 in interior cavity 603 to provide even greater flow rates than those achievable with conventional techniques, thereby greatly enhancing the ability to flush an undesired fluid from the first lumen 512d and reduce the number and size of various bubbles of the undesired fluid that may cling to a surface of the first lumen 512d.

Various methods may be employed to pressurize the liquid 612 in the interior cavity 603 of vessel 602. For example, in some embodiments, various liquid pumps may be employed prior to, or during the establishment of the flow of liquid 612 through the first lumen 512d by pumping liquid 612 into the interior cavity 603 to achieve the necessary pressure(s). In some embodiments, the liquid in the interior cavity 603 is pressurized after the liquid 612 is provided in the first portion 603-1 of the interior cavity 603 (e.g., as per block 902). In some embodiments, the vessel 602 may include a wall portion (for instance, an optional external wall portion 607a shown, e.g., in broken line in FIG. 5E or an optional internal wall portion 607b shown, e.g., in broken line in FIG. 5E), and method 900 may include moving at least part of the wall portion to exert an amount of pressure on the liquid 612 in the first portion 603-1 of the interior cavity 603, the amount of pressure sufficient to cause or at least facilitate or enable the establishing of the flow of at least some of the liquid 612 in the first portion 603-1 of the interior cavity 603 through the first lumen 512d from the second end 512d-1 of the first lumen 512d toward the proximal or first end of the first lumen 512d to flush the fluid other than the liquid 612 from the first lumen 512d.

For example, the vessel 602 may include an exterior wall portion 607a that contacts, is coupled to, or forms a wall of the vessel 602. Wall portion 607a may exhibit a different degree of rigidity or flexibility than other walls of the vessel 602 according to various embodiments. In some embodiments, wall portion 607a may be more flexible or less rigid than other walls of vessel 602. In some embodiments, wall portion 607a may be less flexible or more rigid than other walls of vessel 602. In some embodiments, wall portion 607a forms a piston-like member slidably coupled to vessel 602. In any case, mechanical force may be applied to the exterior wall portion 607a to cause at least part of it to move to exert pressure on the liquid 612 in the first portion 603-1 of the interior cavity 603 when a quantity of the liquid is in the first portion 603-1. For another example, the vessel 602 may include a compliant or semi-compliant interior wall portion 607b (e.g., provided by a flexible membrane) between the first portion 603-1 of the interior cavity 603 and a second portion 603-2 of the interior cavity 603. The second portion 603-2 may be sized to contain at least a quantity of particular fluid other than the liquid 612 concurrently with the liquid 612 received in the first portion 603-1 of the interior cavity 603. A mechanism (e.g., a piston-like member within the vessel 602) may be employed to bear against the interior wall portion 607b to cause at least part of the internal wall portion 607b to move toward the first portion 603-1 and exert pressure on the liquid 612. Alternatively, or in addition, a fluid may be provided into the second portion 603-2 as described herein to cause at least part of the internal wall portion 607b to move toward the first portion 603-1 and exert pressure on the liquid 612 in the first portion 603-1 when a quantity of the fluid is received in the second portion 603-2. It is noted, however, that in some embodiments, liquid 612 is typically incompressible in nature and the induced pressure may fall off rapidly once the flow of the liquid 612 is established though the first lumen 512d. Accordingly, the pressure induced on the liquid 612 may need to be repeatedly reestablished as the flow of the liquid proceeds or continues. In some embodiments, the wall portion 607b may be provided by a moveable piston-like member within the vessel 602. In some embodiments, the wall portion 607b may be provided by a flexible membrane.

Use of the internal wall portion 607b may be motivated by various reasons including segregating the particular fluid in the second portion 603-2 of the interior cavity from the liquid 612 in the first portion 603-1 of the interior cavity (e.g., to prevent intermixing or cross-contamination thereof).

Figure 8B:
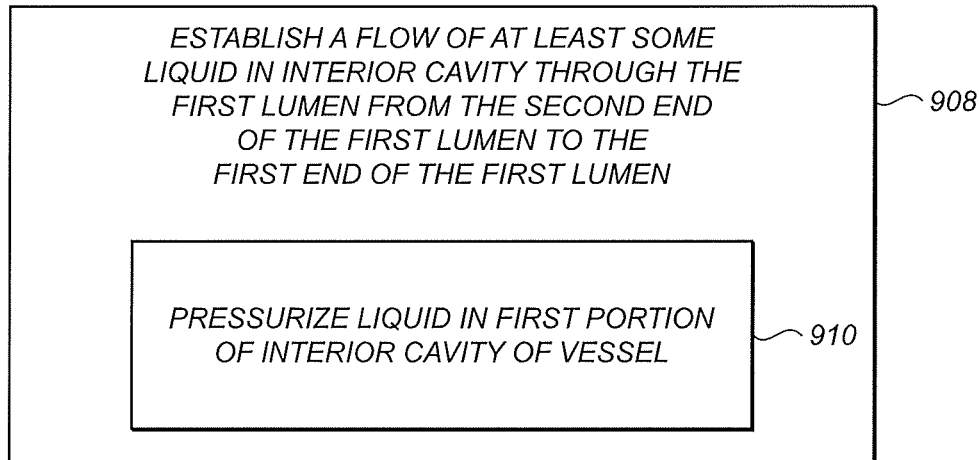
FIG. 8B illustrates an exploded view of a portion of the method of FIG. 8A, according to some example embodiments.
Figure 8C:
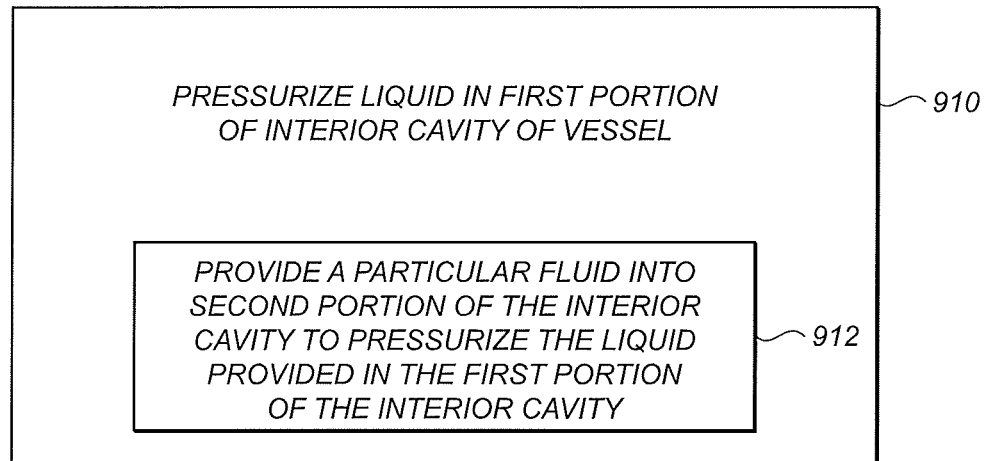
FIG. 8C illustrates an exploded view of a method block or element of FIG. 8B, according to some example embodiments.

FIG. 8C includes some sub-actions associated with block 910 of FIG. 8B to pressurize the liquid 612 in the first portion 603-1 of the interior cavity 603 of the vessel 602. Block 912 includes instructions to provide a quantity of a particular fluid into a second portion of the interior cavity 603 to pressurize the liquid 612 provided in the first portion 603-1 of the interior cavity 603. In some embodiments, the particular fluid is the same as the liquid 612. For example, additional quantities of the liquid 612 may be pumped into the interior cavity 603 to pressurize the liquid 612 in the first portion 603-1, for example, as described above. In some embodiments, the particular fluid is different than the liquid. For example, the particular fluid may be a gas. In some embodiments, the particular fluid is a compressible fluid while the liquid 612 is an incompressible liquid. In various embodiments, the quantity of the particular fluid provided to the second portion 603-2 according to block 912 is sufficient to exert an amount of pressure on the liquid 612 in the first portion 603-1 of the interior cavity 603 to cause or at least facilitate or enable the establishing of the flow of at least some of the liquid 612 in the first portion 603-1 of the interior cavity 603 through the first lumen 512d from the second or distal end 512d-1 of the first lumen 512d toward the first or proximal end of the first lumen 512d to flush undesired fluid (e.g., air) different than the liquid 612 at least from the first lumen 512d. It should be noted that the actions of block 912 may be performed with or without either or both of the wall portions 607a, 607b. For example, the internal wall portion 607b is not necessary in some embodiments where the particular fluid is added to the second portion 603-2, because the mere addition of the particular fluid to the second portion 603-2 will act to increase pressure on the liquid 612 already present in the first portion 603-1.

It should also be noted that the volume and location thereof of the second portion 603-2 of the interior cavity 603 and the volume and location thereof of the first portion 603-1 of the interior cavity may be transient in nature at least during the flushing of the first lumen 512d. In some embodiments where the particular fluid is a gas and the internal wall portion 607b does not exist, the volume of the second portion 603-2 and the location thereof may be defined as the volume of space occupied by the gas within the interior cavity 603 of the vessel 602, and the volume of the first portion 603-1 and the location thereof may be defined as the volume of space occupied by the liquid 612 within the interior cavity 603 of the vessel 602, the volumes of space occupied by the first and second portions 603-1, 603-2 varying at least during the flushing of the first lumen 512d. Even in embodiments where the internal wall portion 607b is present, the volumes of space occupied by the first and second portions 603-1, 603-2 may vary due to movements of the interior wall portion 607b at least during the flushing of the first lumen 512d.

Figure 5D:
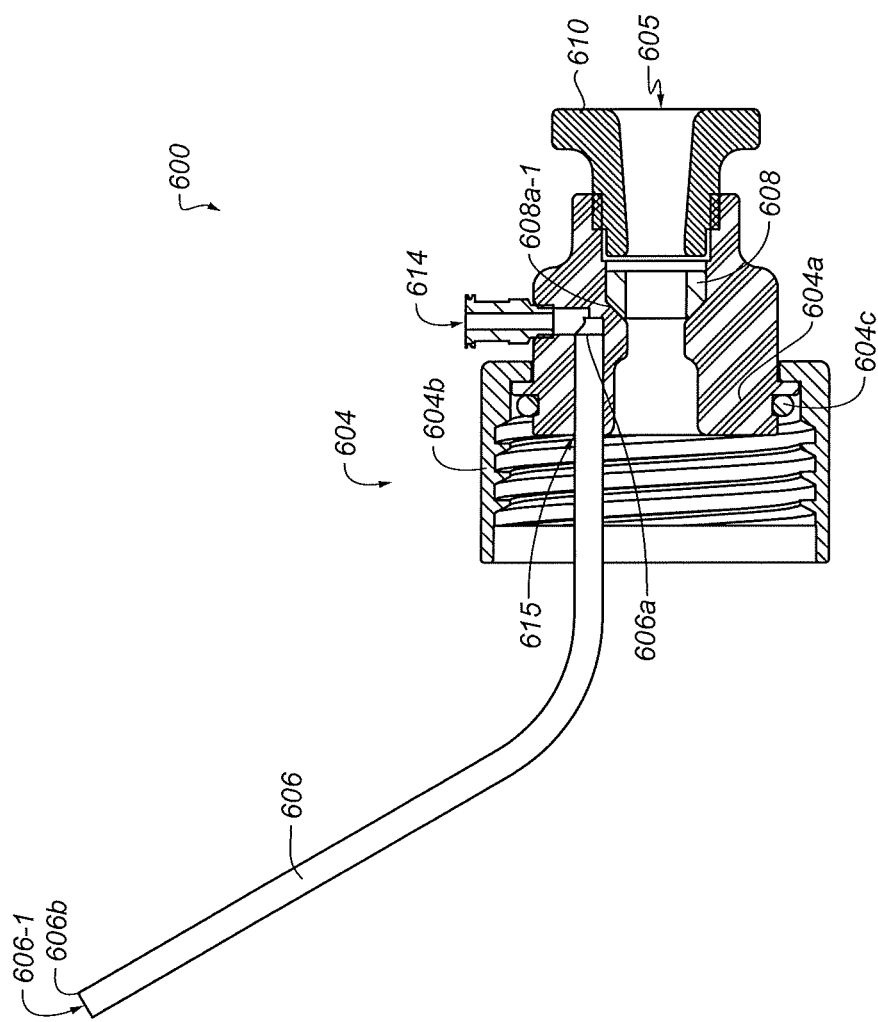
FIG. 5D is a cutaway diagram of the cap of FIG. 5B, according to some example embodiments.
Figure 5E:
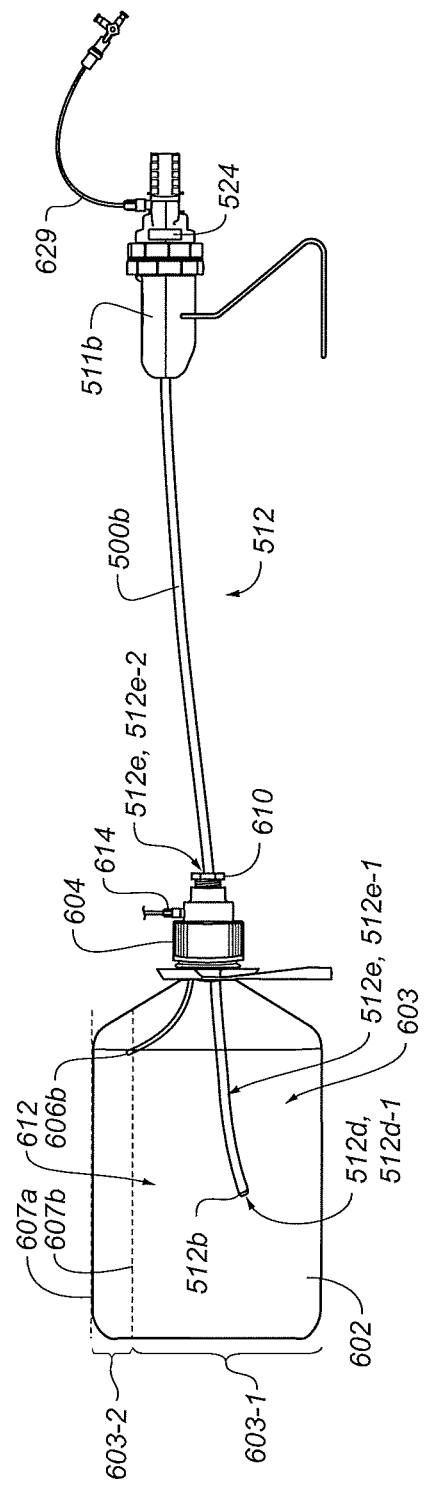
FIG. 5E illustrates a portion of the flushing kit of FIG. 5A in a configuration to flush a catheter system, such as a portion of the catheter system of FIG. 4A, according to some example embodiments.
Figure 5F:
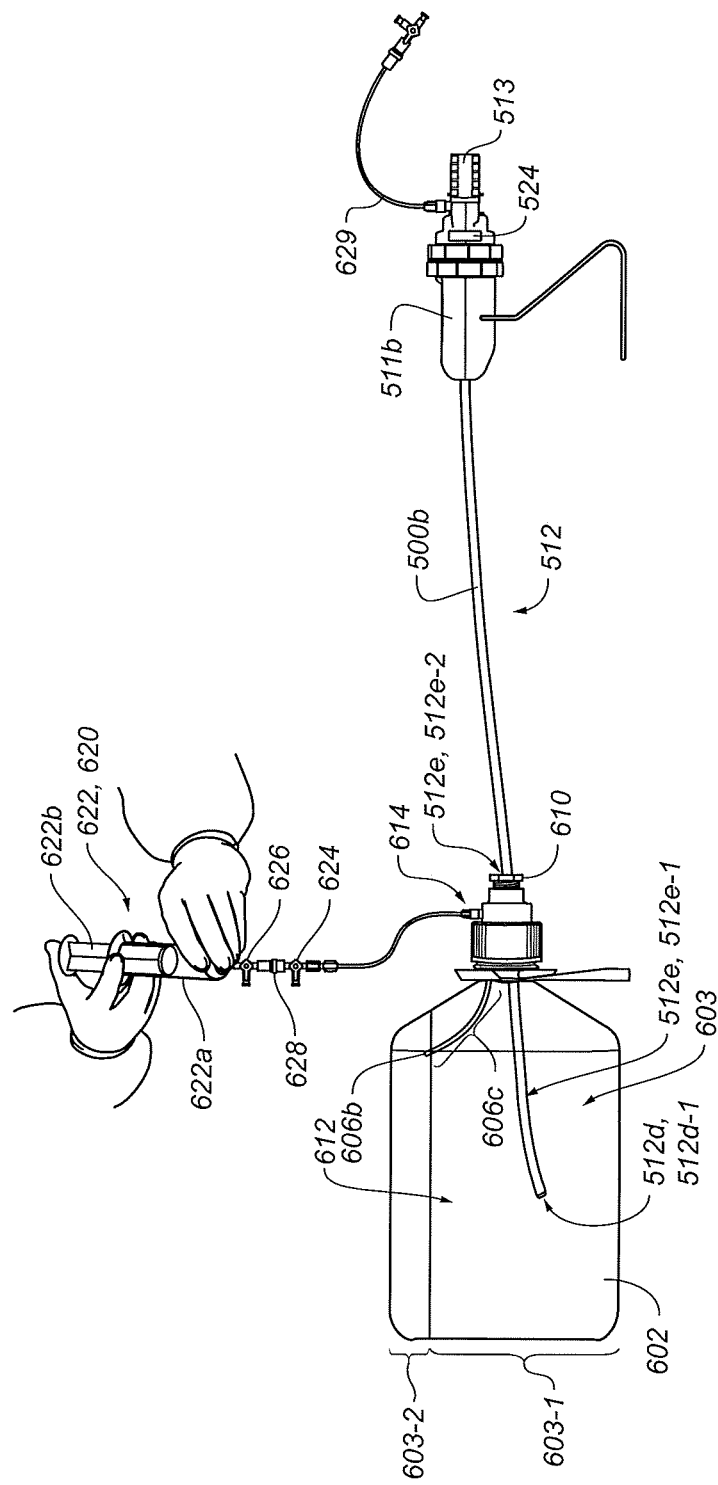
FIG. 5F illustrates the flushing kit of FIG. 5A in a configuration to flush a catheter system, such as a portion of the catheter system of FIG. 4A, according to some example embodiments.
Figure 5G:
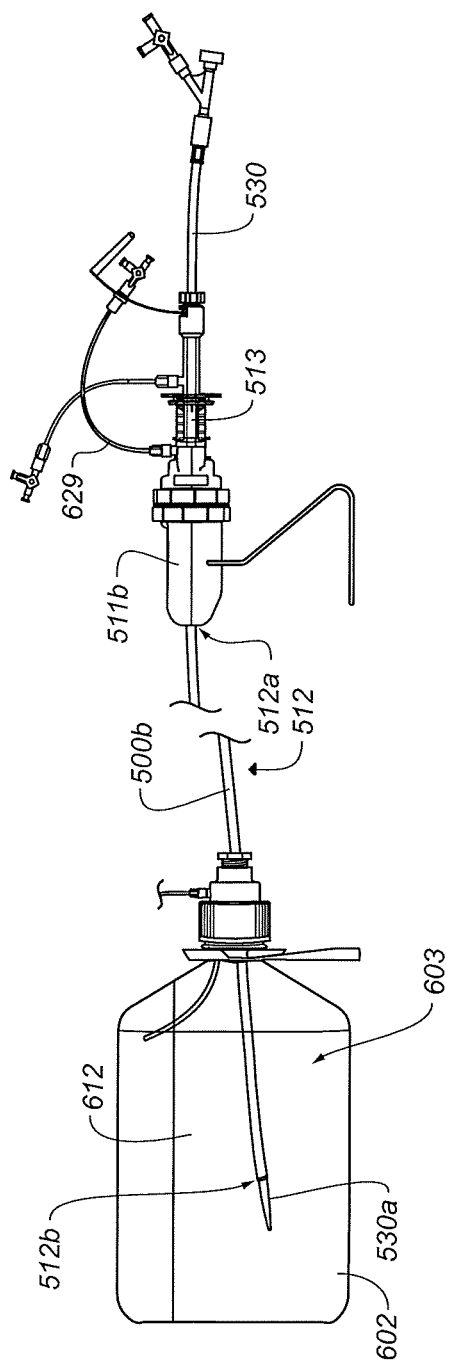
FIG. 5G illustrates a portion of the flushing kit of FIG. 5A in a configuration to flush a catheter system, such as a portion of the catheter system of FIG. 4A, according to some example embodiments.

FIG. 8D includes a method 900A for providing a quantity of particular fluid other than the liquid 612 into a second portion of the interior cavity 603 while at least some of the liquid 612 is in the first portion 603-1 of the interior cavity 603. In some embodiments, vessel 602 includes a second port in fluid communication with the interior cavity 603, the second port other than the first port 605 (i.e., the first port 605 and the second port being different ports). In some embodiments, such second port is considered to not be part of the vessel 602. Block 920 includes instructions to provide, via the second port, a quantity of particular fluid other than the liquid 612 into the second portion 603-2 of the interior cavity 603 while at least some of the liquid 612 is in the first portion 603-1 of the interior cavity 603. For example, FIG. 5F shows the introduction of a particular fluid (e.g., air) other than the liquid 612 into the second portion 603-2 of the interior cavity 603, the particular fluid introduced via a second port other than the first port 605 in which the distal end portion 512e of the elongate shaft member 500b is introducible. FIG. 5D shows a sectioned view of cap 604 providing various ports including the first port 605, each of the various ports positionable in fluid communication with the interior cavity 603 of the vessel at least in a state in which cap 604 is secured to vessel 602. In some embodiments (e.g., embodiments in which conduit member 606 (i.e., described below) is not employed), port 614 provided by the cap 604 may be considered to be the second port in fluid communication with the interior cavity 603 of the vessel 602. In some embodiments (e.g., embodiments in which conduit member 606 (i.e., described below) is not employed), port 615 provided by the cap 604 may be considered to be the second port in fluid communication with the interior cavity 603 of the vessel 602. It is noted that in some embodiments, the second port (e.g., 614, 615) may be in fluid communication with, or may be in contact with, the liquid 612 in the first portion 603-1 of the interior cavity 603. In this regard, the particular fluid delivered to the second portion 603-2 of the interior cavity 603 may travel through the liquid 612. For example, when the particular fluid is a gas (e.g., air), a bubble stream of the gas may flow through the liquid 612 from the second port (e.g., 614, 615) to the second portion 603-2 of the interior cavity 603. In some embodiments, at least the first port 605, the second port (e.g., 614 or 615), or both are provided in the cap 604.

In some embodiments, the vessel 602 or the flushing kit 600 includes a conduit member 606 arranged to fluidly communicate with a source 620 of particular fluid, and includes a first conduit end 606a, a second conduit end 606b, and a second lumen 606-1 extending between the first conduit end 606a and the second conduit end 606b. It may also be stated that the second lumen 606-1 extends from the first conduit end 606a to the second conduit end 606b. In some embodiments, the above-discussed second port is provided by the first conduit end 606a or the second conduit end 606b. In various embodiments, a flow of the particular fluid is conveyed from the source 620 of the particular fluid though the second lumen 606-1 of the conduit member 606 toward the second conduit end 606b of the conduit member 606. In some embodiments, the first conduit end 606a is arranged to receive the particular fluid from the source 620 of the particular fluid, and the second lumen 606-1 is arranged to convey a flow of the particular fluid toward the second conduit end 606b. In various embodiments, the second conduit end 606b is arranged to provide the particular fluid into the second portion 603-2 of the interior cavity 603. For example, FIG. 5F shows that the conduit member 606 is arranged to locate the second conduit end 606b in the second portion 603-2 of the interior cavity 603 of the vessel 602. According to various embodiments, conduit member 606 is arranged to locate the second conduit end 606b at a location in the interior cavity 603 away from the liquid 612 in the first portion 603-1 of the interior cavity 603. In some embodiments, the second conduit end 606b may be positioned to avoid contact with liquid 612 in the first portion 603-1 of the interior cavity 603.

In some embodiments, at least part (e.g., part 606c shown in FIG. 5F) of the conduit member 606 is arranged to extend across at least part of the first portion 603-1 of the interior cavity 603 as shown in FIG. 5F by way of non-limiting example. In some embodiments, the at least part of the conduit member 606 extending across the at least part of the first portion 603-1 of the interior cavity 603 contacts, or is wetted by, the liquid 612 in the first portion 603-1 of the interior cavity 603. As can be visualized with respect to FIG. 5D, the second lumen 606-1 of conduit member 606 is arranged to avoid receiving the distal end portion 512e of the elongate shaft member 500b when the distal end portion 512e of the elongate shaft member 500b is received in the first port 605. Stated another way, in some embodiments, the second lumen 606-1 of conduit member 606 is arranged to prevent any reception of the distal end portion 512e of the elongate shaft member 500b when the distal end portion 512e of the elongate shaft member 500b is inserted into the interior cavity 603 via the first port 605. That is, first port 605 and any of the ports provided by the first and second conduit ends 606a, 606b are not collinearly arranged to concurrently allow the distal end portion 512e to pass through all of these ports. In some embodiments, the second lumen 606-1 may be sized or include a size too small to allow the distal end portion 512e of the elongate shaft member 500b to pass through (e.g., as shown in FIG. 5D).

In view of the above, it should be noted that the above-discussed second port may be provided by port 614, port 615, the first conduit end 606a, or the second conduit end 606b. In some embodiments, the second port is arrangeable to fluidly communicate with a particular fluid in the second portion 603-2 of the interior cavity 603, the particular fluid other than the liquid 612. In some embodiments, the second port is arranged to fluidly communicate with a source 620 of the particular fluid other than the liquid 612 and provide the particular fluid into the second portion 603-2 of the interior cavity 603 to pressurize the liquid 612 in the first portion 603-1. In some embodiments, the second port is arranged to prevent any reception of the distal end portion 512e of the elongate shaft member 500b when the distal end portion 512e of the elongate shaft member 500b is inserted into the interior cavity 603 via the first port 605. The second port may be arranged to avoid receiving the distal end portion 512e of the elongate shaft member 500b when the distal end portion 512e of the elongate shaft member 500b is received in the first port 605. That is, at least the second port may be positioned to avoid receiving the distal end portion 512e of the elongate shaft member 500b when the distal end portion 512e of the elongate shaft member 500b is received in the first port 605, or the second port may have a size too small to receive the distal end portion 512e of the elongate shaft member 500b. In some embodiments, the second port is positioned or is positionable to permit a flow of the particular fluid through the second port while concurrently preventing a flow of the liquid 612 through the second port. This configuration may exist at least during or in a state in which the particular fluid is provided per block 920 or the liquid 612 is pressurized per block 912. For example, when the second port is provided by the second conduit end 606b, the second port may be positioned away from the liquid 612 in the first portion 603-1 of the interior cavity, thereby allowing a flow of the particular fluid through the second port while concurrently preventing a flow of the liquid 612 through the second port.

Referring back to FIG. 5F, source 620 of the particular fluid may be provided at least in part by syringe 622 and may be employed according to blocks 912, 920 as per some example embodiments. In FIG. 5F, a first valve 624, a second valve 626, and a check valve 628 are operatively coupled between source 620 of the particular fluid (e.g., syringe 622) and the second port (e.g., 606a, 606b, 614, or 615) to control a flow of the particular fluid from the source 620 to at least the second port in accordance with various embodiments. In some embodiments, the valves 624, 626, and 628 are considered part of the source 620 and not part of the kit 600 shown in FIG. 5A. In various embodiments, the first valve 624 is operatively coupled or arranged between port 614 or the first conduit end 606a and the source 620 (e.g., syringe 622). In various embodiments, the second valve 626 is operatively coupled or arranged between port 614 or the first conduit end 606a and the source 620 (e.g., syringe 622). In some embodiments, the second valve 626 is operatively coupled or arranged between the check valve 628 and the source 620 of the particular fluid. In various embodiments, the check valve 628 is operatively coupled or arranged between the source 620 of the particular fluid and the first valve 624.

According to some embodiments, each of the first valve 624 and the second valve 626 is selectively operable in a first state in which the particular fluid is allowed to flow via the second port (or conduit member 606 in applicable embodiments) from the source 620 (e.g., syringe 622) of the particular fluid to the second portion 603-2 of the interior cavity 603. In some embodiments, each of the first valve 624 and the second valve 626 is selectively operable in a second state in which the particular fluid is restricted from flowing via the second port (or conduit member 606 in applicable embodiments) from the source 620 of the particular fluid to the second portion 603-2 of the interior cavity 603. In some embodiments, at least the first valve 624 is selectively operable in a third state in which the particular fluid is restricted from flowing via the second port (or conduit member 606 in applicable embodiments) from the source 620 (e.g., syringe 622) of the particular fluid to the second portion 603-2 of the interior cavity 603, but is allowed to flow via the second port (or conduit member 606 in applicable embodiments) from the second portion 603-2 of the interior cavity 603 to a particular location located away from the source 620 of the particular fluid, the particular location not located in (a) the interior cavity 603, (b) the elongate shaft member 500b, or (a) and (b). For example, this functionality may be provided when the first valve 624 is a three-way valve. In some embodiments, the second valve 626 is a three way valve. In some embodiments, both the first valve 624 and the second valve 626 are each provided by a respective three way valve.

According to some embodiments, the check valve 628 is operable to restrict at least a flow of the particular fluid from the first valve 624 toward the source 620 (e.g., syringe 622) of a fluid such as the particular fluid. In various embodiments, the check valve 628 is operatively coupled between the first valve 624 and the second valve 626 to allow a flow of the particular fluid in a direction from the second valve 626 toward the first valve 624, but to restrict a flow of the particular fluid in a direction from the first valve 624 toward the second valve 626.

According to various embodiments, the particular fluid may be provided to the second portion 603-2 of the interior cavity 603 at least by manipulating the first valve 624 to provide an unrestricted pathway between the source 620 (e.g., syringe 622) of the particular fluid and the second portion 603-2 of the interior cavity 603 (for example, the first state described above). If the particular fluid is present in tube 622a (at least FIG. 5F) of the syringe 622, the second valve 626 is also manipulated to provide an unrestricted pathway between the source 620 (e.g., syringe 622) of the particular fluid and the second portion 603-2 of the interior cavity 603 (for example, the first state described above), and the plunger 622b of the syringe 622 is pushed or advanced to cause the particular fluid to flow (e.g., via the second port or conduit member 606) into the second portion 603-2 of the interior cavity 603. In some embodiments, the amount of particular fluid provided in the tube 622a provides a desired amount of the particular fluid to the second portion 603-2 of the interior cavity 603. In other embodiments however, additional amounts of the particular fluid are required. In some embodiments in which the second valve 626 is a three-way valve, the second valve 626 is operated in a state similar to the third state described above with respect to first valve 624, the third state associated with the second valve 626 allowing for, or creating another flow path between the source 620 and another source of the particular fluid (e.g., the surrounding atmosphere) which allows a free additional supply of the particular fluid to be provided into the tube 622a as the plunger 622b is retracted. It is noted that the check valve 628 prevents the particular fluid from being withdrawn from the second portion 603-2 of the interior cavity 603 during the retraction of the plunger 622b according to various embodiments.

According to various embodiments, once the syringe 622 has been recharged or resupplied with the particular fluid, the second valve 626 is again operated to provide an unrestricted pathway between the source 620 (e.g., syringe 622) of the particular fluid and the second portion 603-2 of the interior cavity 603 (for example, the first state described above), and the plunger 622b is advanced to provide the particular fluid to the second portion 603-2 of the interior cavity 603. This procedure may be repeated until a desired quantity of the particular fluid has been delivered to the second portion 603-2 of the interior cavity 603 of vessel 602, e.g., according to blocks 912 or 920.

According to various embodiments, the second portion 603-2 of the interior cavity 603 is sized to receive at least a quantity of particular fluid sufficient to exert an amount of pressure on the liquid 612 in the first portion 603-1 of the interior cavity 603, the amount of pressure sufficient to cause movement of at least some of the liquid 612 in the first portion of the interior cavity 603 into the second end 512d-1 of the first lumen 512 and flush the first lumen of the fluid other than the liquid 612 in the direction through the first lumen 512d extending from the second end 512d-1 of the first lumen 512d toward the first or proximal end of the first lumen 512d. It is noted that the valve 624 may be manipulated to prevent a flow of the liquid 612 though the lumen 512d when the quantity of the particular fluid is provided to the second portion 603-2 of the interior cavity 603 to pressurize the liquid 612 in the first portion 603-1 of the interior cavity 603. Once the liquid 612 in the first portion 603-1 of the interior cavity 603 has been adequately pressurized, valve 524 may be manipulated to allow for the flow of the liquid 612 through the first lumen 512d to flush a fluid other than the liquid 612 that may reside in the first lumen 512d.

It is noted that relatively large pressures may be developed in the liquid stored in the first portion 603-1 of the interior cavity 603, and that these relatively large pressures, when combined with the direct entry of the liquid 612 into the distal end 512d-1 of the first lumen, provide for enhanced flushing capabilities. It is further noted that, when the particular fluid is provided in the second portion 603-2 of the interior cavity 603, the vessel 602 acts as a hydraulic accumulator or pressure storage reservoir in which the liquid 612 is held under pressure by the pressurized particular fluid (e.g., air). The accumulator enables the system to better respond to the flushing action during removal of any undesired fluids from the first lumen 512d. In various embodiments, the accumulator may be employed to reduce or smooth out pulsations that may arise in a flow of the liquid 612.

After the flushing of the lumen 512d has been completed, the elongate shaft member 500b is removed from the vessel 602, for example, to allow for a subsequent delivery of the elongate shaft member 500b through a bodily opening as described above. However, it is noted that any remaining liquid 612 in the first portion 603-1 of the interior cavity 603 may still be under pressure. If the elongate shaft member 500b was to be removed from the vessel 602 under this pressurized condition, at least some of the liquid 612 in the first portion 603-1 of the interior cavity 603 would likely erupt outwardly from the vessel 602 and possibly spray a user (e.g., a health care practitioner) or various equipment. This is, understandably, an undesired outcome, especially when the vessel 602 acts a hydraulic accumulator that still may be storing relatively high levels of energy. Accordingly, in some embodiments, liquid 612 in the first portion 603-1 of the interior cavity 603 is depressurized prior to the removal of the elongate shaft member 500b from vessel 602. In various embodiments, in which particular fluid other than the liquid 612 has been provided to second portion 603-2 of the interior cavity 603 to pressurize the liquid 612, liquid 612 is depressurized by removing the particular fluid from or otherwise depressurizing the particular fluid in the second portion 603-2 of the interior cavity 603. In some embodiments associated with FIG. 5F, this removal or otherwise depressurizing may be accomplished by manipulating the first valve 624 (e.g., a three-way valve) into a particular state (e.g., the third state associated with first valve 624 described above) to permit a flow (e.g., via the second port or the conduit member 606) of the particular fluid from the second portion 603-2 of the interior cavity 603 to a location where the particular fluid can be released, drained, discharged, or dispersed. For example, when the particular fluid is air or some other gas, the first valve 624 may be manipulated to divert the particular fluid to atmosphere and, thus, depressurize the particular fluid in the second portion 603-2 and the liquid 612 in the first portion 603-1 of the interior cavity 603. It is noted that dispersing a particular fluid, such as air, to the atmosphere or the surrounding environment to reduce the pressure within the interior cavity 603 of the vessel 602, instead of dispersing the liquid 612 to reduce the pressure, avoids the negative effects associated with an eruption of the liquid 612 as discussed above. In some embodiments, elongate shaft member 500b may then be removed from the vessel 602 by first manipulating seal engaging member 610 to unseal the exterior surface of the distal end portion 512e of the elongate shaft member 500b from the vessel 602. This unsealing may occur at least prior to a delivery of at least the distal end portion 512e of the elongate shaft member 500b through a bodily opening leading to a bodily cavity. Separation or removal of the elongate shaft member 500b from the vessel 602 may occur at least prior to a delivery of at least the distal end portion 512e of the elongate shaft member 500b through a bodily opening leading to a bodily cavity.

It is noted in various embodiments in which liquid 612 in the first portion 603-1 of the interior cavity 603 is depressurized by the depressurizing of the particular fluid in the second portion 603-2 of the interior cavity 603, it is advantageous to avoid contact between the liquid 612 and the depressurizing flow path of the particular fluid since this would likely result in at least some of the liquid 612 being sprayed into the atmosphere or the surrounding environment with the ejected particular fluid. Accordingly, in some embodiments, the second port is positioned to permit a flow of the particular fluid from the second portion 603-2 of the interior cavity 603 through the second port while concurrently preventing a flow of the liquid 612 from the first portion 603-1 of the interior cavity 603 through the second port at least during a state in which the liquid 612 in the first portion 603-1 of the interior cavity 603 undergoes a reduction in pressure. For example, when the second port is provided by the second conduit end 606b of the conduit member 606, the second conduit end 606b is positioned to avoid contact with liquid 612 in the first portion 603-1 of the interior cavity 603, and thus allows for the removal of the particular fluid from the second portion 603-1 of the interior cavity 603 without removal of at least some of the liquid 612. In some embodiments, at least a portion of a wall member (e.g., interior wall portion 607b) positioned between the first portion 603-1 of the interior cavity 603 and the second portion 603-2 of the interior cavity 603 may be employed to separate the liquid 612 from the flow path that removes the particular fluid from the second portion 603-2 of the interior cavity 603.

In some embodiments, the vessel 602 is positionable to permit a flow of the particular fluid from the second portion 603-2 of the interior cavity 603 through the second port while concurrently preventing a flow of the liquid 612 from the first portion 603-1 of the interior cavity 603 through the second port at least during a state in which the liquid 612 in the first portion 603-1 of the interior cavity 603 undergoes a reduction in pressure. For example, in some embodiments in which conduit member 606 is not employed, the second port may be provided by, for example, a port located in cap 604 (e.g., second port 615). In some embodiments, the vessel 602 may be positioned such that the second port (e.g., 615) is submerged partially or fully in the liquid 612 at a time in which the particular fluid in the second portion 603-2 of the interior cavity is to be depressurized. According to some embodiments, vessel 602 may be manipulated (e.g., tilted) to position a surface level of the liquid 612 away from the second port (e.g., 615) to allow the particular fluid to be removed via the second port from the second portion 603-2 of the interior cavity without contacting the liquid 612. It is noted in various embodiments that the particular fluid is provided to, and removed from, the second portion 603-2 of the interior cavity 603 via a same second port. In other embodiments, the particular fluid is provided to the second portion 603-2 of the interior cavity 603 via the second port, and the particular fluid is removed from the second portion 603-2 of the interior cavity 603 via a third port provided in or by the vessel 602, the third port other than the second port, and the third port other than the first port 605 in which at least part of the distal portion (e.g., 510e, 512e) of the elongate shaft member (e.g., 500a, 500b) is inserted. In various embodiments, the first port 605, the second port, and the third ports are different ports. In yet other embodiments, the particular fluid is removed from the second portion 603-2 of the interior cavity 603 via the second port, and the particular fluid is provided to the second portion 603-2 of the interior cavity 603 via a third port provided in the vessel 602, the third port other than the second port and each of the second and third ports other than the first port 605. In various embodiments, the first port 605, the second port, and the third ports are different ports. In some embodiments, the third port is provided by the second port.

In some embodiments, after the first lumen 512d has been flushed of a fluid other than the liquid 612, a dilator may be introduced into the first lumen 512d to provide a catheter sheath/dilator assembly that may be subsequently delivered (e.g., percutaneously or intravascularly) through a bodily opening leading to a bodily cavity. For example, in FIG. 5G a dilator assembly 530 has been inserted into the first lumen 512d of the elongate shaft member 500b of catheter sheath 512 from the proximal end 512a of the elongate shaft member 500b to the distal end 512b of the elongate shaft member 500b. A tip portion 530a of the dilator assembly 530 is shown protruding into the interior cavity 603 of the vessel 602. Advantageously, any liquid 612 in the first lumen 512d that may be pushed out of the first lumen 512d by the inserted dilator assembly 530 is supplanted or otherwise replaced by liquid 612 in the interior cavity 603. It is noted that liquid 612 in the interior cavity 603 resists expulsion of liquid 612 in first lumen 512d during the insertion of the dilator assembly 530 into the first lumen 512d. Any undesired fluid that is introduced into the first lumen 512d during the insertion of the dilator assembly 530 into the first lumen 512d may be flushed out of the first lumen 512d via flushing techniques similar to or identical to those taught above in this disclosure. It is noted that the dilator assembly 530 may be removed at least partially from the first lumen 512d during subsequent flushing thereof.

According to some embodiments, before or after the elongate shaft member 500b is flushed according to the discussions above, various lumens in the elongate shaft member 500a may be flushed according to a same or similar procedure as that set forth above with respect to flushing of the elongate shaft member 500b. In this regard, FIG. 6 illustrate, among other things, the flushing of various lumens of the elongate shaft member 500a of the catheter 510 as well as the removal of undesired fluid from various other parts of the catheter 510, according to some embodiments. Procedures or structures not differentiated in FIG. 6 or the accompanying descriptions below are the same or substantially the same as those discussed above or illustrated with respect to figures already described.

Figure 6A:
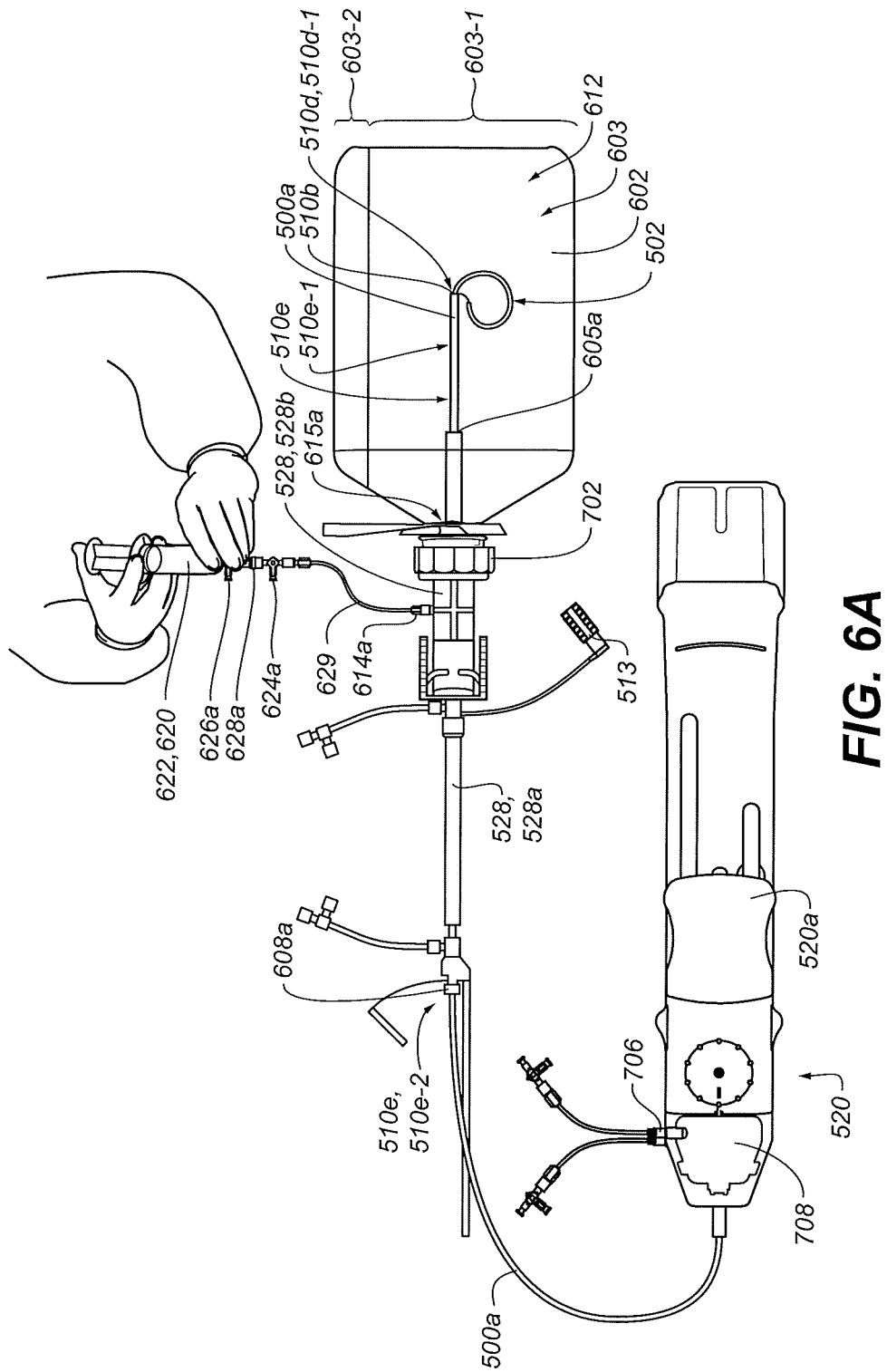
FIG. 6A illustrates a catheter system in a flushing configuration, according to some example embodiments.

As shown in FIG. 6A, the elongate shaft member 500a may be inserted through a lumen of a loading assembly 528 to place a second part 510e-1 of the elongate shaft member 500a, which comprises the distal end 510b, into the interior cavity 603 of the vessel 602. According to some embodiments, a proximal portion 528a of the loading assembly 528 may be removably or detachably coupled with a distal portion 528b of the loading assembly 528 in a state where the cap 513 of the proximal portion 528a is removed. According to various embodiments, a pathway is provided between the physically coupled proximal portion 528a of the loading assembly 528 and distal portion 528b of the loading assembly 528b, the passageway extending between a first interior lumen of the proximal portion 528a and a first interior lumen of the distal portion 528b. The distal portion 528b of the loading assembly 528 may be threadedly engaged to the vessel 602 by tightening of a threaded coupler 702. In this regard, the loading assembly 528, (e.g., including the threaded coupler 702) may correspond to the removable cap 604 discussed above, and for at least this reason, may also form part of the vessel 602. Accordingly, in some embodiments, an end of the first interior lumen of the distal portion 528b of the loading assembly 528 may be considered to correspond to the first port 605 discussed above. Alternatively, in some embodiments, an end of the interior lumen of the proximal portion 528a of the loading assembly 528 may form a port 605a shown in FIG. 6A, and port 605a may be considered to correspond to the first port 605 discussed above.

The distal portion 528b of the loading assembly 528 may include a port 614a that may correspond to the port 614 discussed above. Similarly, valves 626a, 628a, and 624a may correspond to valves 626, 628, and 624, discussed above, and may be coupled to the distal portion 528b of the loading assembly 528 via tube 629 to provide fluid to or receive fluid from the port 614a. Also, a port 615a may correspond to port 615, discussed above, and may fluidly communicate with the port 614a. In this regard, the fluid communication channel or "second lumen" between ports 614a and 615a provided by the distal portion 528b may be distinct from either of the first lumen of the proximal portion 528a of the loading assembly 528 or the first lumen of the distal portion 528b of the loading assembly 528 through which the distal end portion 510e of the elongate shaft member 500a is inserted, like the configuration of the cap 604 discussed above.

In some embodiments, a first part 510e-2 of the distal end portion 510e may correspond to the first part 512e-2 of the distal end portion 512e, discussed above. Accordingly, an exterior surface of the first part 510e-2 may be selectively sealed by a seal 608a, which may correspond to the seal 608 discussed above. In this regard, the seal 608a may be within a threaded coupling that, when turned, compresses the seal 608a against the exterior surface of the first part 510e-2 of the distal end portion 510e of the elongate shaft member 500a to seal the first part 510e-2 to a portion of the loading assembly 528. Also in this regard, the loading assembly 528 may be considered part of the vessel 602 in some embodiments, for example, in the configuration of at least FIG. 6A, where the loading assembly 528 is coupled to the vessel 602 via distal portion 528b. In at least some of these embodiments, it may be considered that the seal 608a selectively seals a cylindrical exterior surface of the first part 510e-2 of the distal end portion 510e to at least part of the vessel 602.

With at least the configuration shown in FIG. 6A, liquid 612 in the interior cavity 603 of the vessel 602 may be caused, according to the procedures discussed above, to flow through the first lumen 510d of the elongate shaft member 500a from the second or distal end 510d-1 of the first lumen 510d toward or to the first or proximal end of the first lumen 510d (within the housing 520) to flush a fluid other than the liquid from the first lumen 510d. In this regard, according to some embodiments, the liquid that proceeds into the housing 520 from the first or proximal end of the first lumen 510d may proceed into an interior chamber 708 of the housing 520 and then be released via a port, such as port 706.

In some embodiments, where a manipulable portion 502 is provided, the manipulable portion 502 may be delivered in its unexpanded configuration via the first port (e.g., port 605a) into the first portion 603-1 of the interior cavity 603. FIG. 6A illustrates a state according to some embodiments, where the manipulable portion 502 has been delivered into the first portion 603-1 of the interior cavity 603.

Figure 6B:
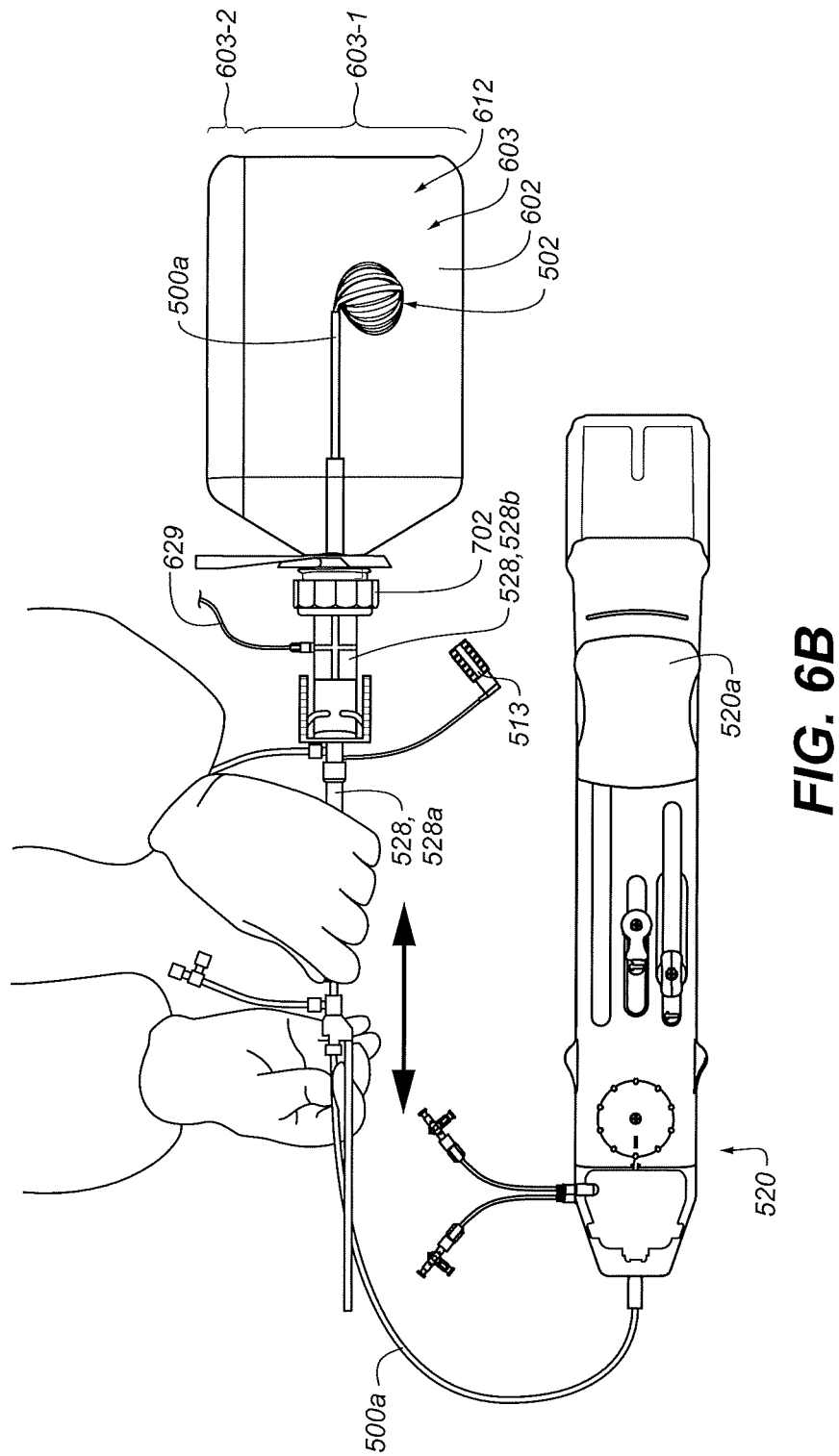
FIG. 6B illustrates removal of undesired fluid from a manipulable portion of a catheter system, according to some example embodiments.
Figure 7A:
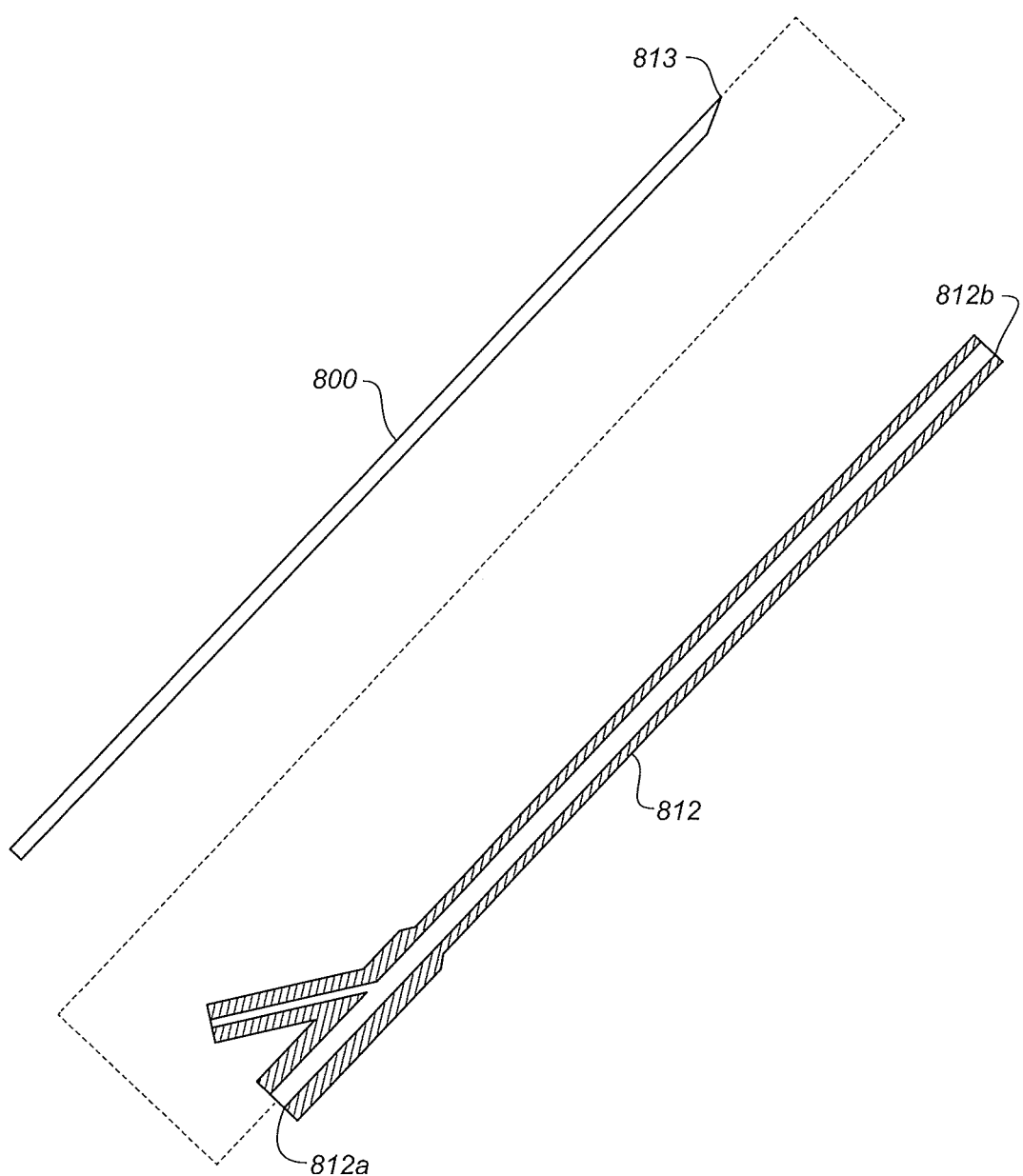
FIG. 7A is a schematic that shows at least part of a conventional catheter system.
Figure 7B:
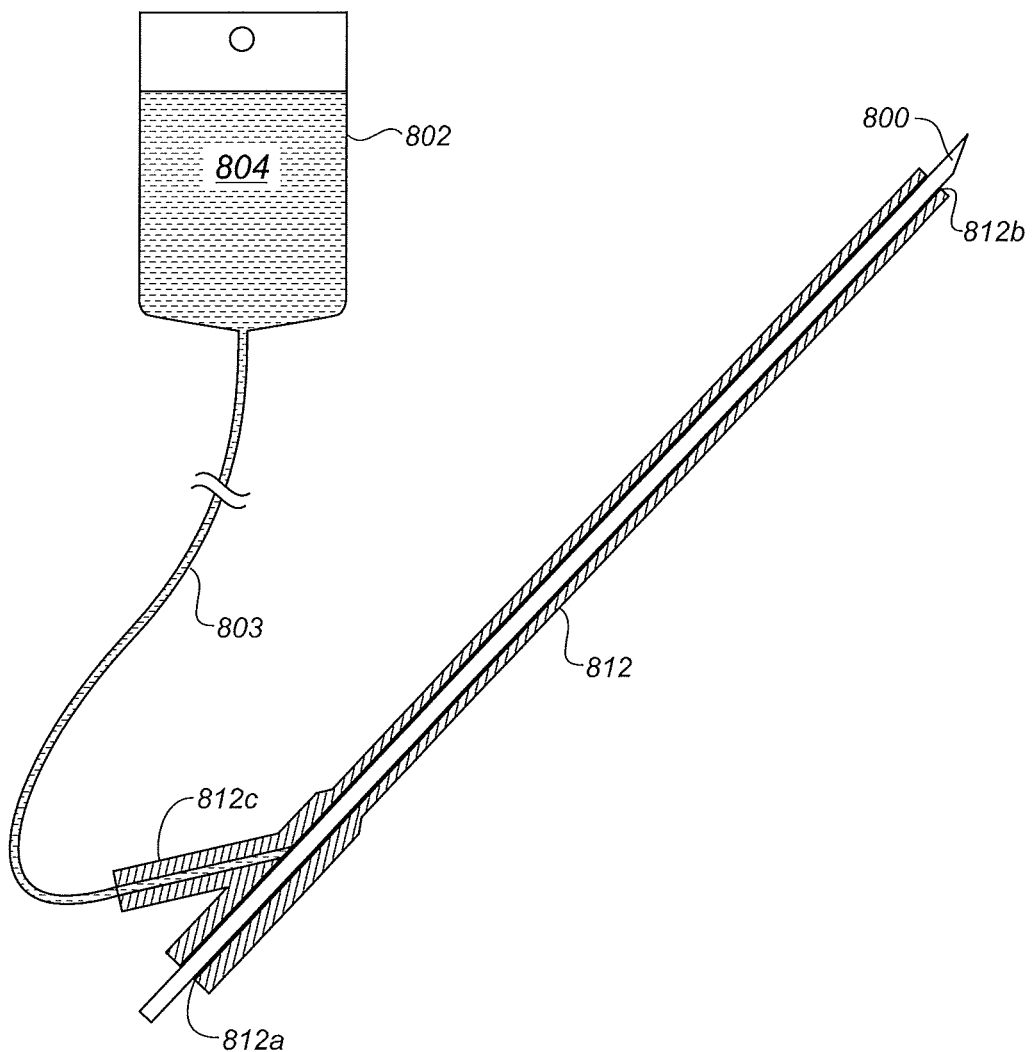
FIG. 7B illustrates a typical flushing procedure employed by conventional catheter systems.

The manipulable portion 502 itself may present a risk of trapping air or other undesired fluid. For example, the manipulable portion 502 may include a plurality of elements or members (e.g., elongate members 304, 504) that converge, overlap, or otherwise create regions capable of entrapping air or other undesired fluid. Accordingly, the manipulable portion 502, in some embodiments, is moved into the expanded configuration, as shown in FIG. 6B, in the first portion 603-1 of the interior cavity 603 to, for example, facilitate removal of any entrapped air or undesired fluid. In this regard, the manipulable portion 502 is selectively moveable from an unexpanded configuration, in which the manipulable portion 502 is sized for delivery through the first port (e.g., 605a) and an expanded configuration in which the manipulable portion 502 is sized too large for delivery through the first port (e.g., 605a). In some embodiments, the movement from the unexpanded configuration to the expanded configuration is facilitated by a sliding of the actuator 520a from a first position shown in FIG. 6A to a second position shown in FIG. 6B. In some embodiments, when the manipulable portion 502 is in the expanded configuration in the first portion 603-1 of the interior cavity 603, the manipulable portion 502 is repeatedly moved, for example, by the hand movements shown in FIG. 6B, to agitate the liquid 612 in the first portion 603-1 of the interior cavity 603. In some embodiments, the manipulable portion 502 may be repeatedly moved from the unexpanded or delivery configuration to the expanded or deployed configuration and then back to the unexpanded or delivery configuration in the first portion 603-1 of the interior cavity 603 while the manipulable portion 502 is wetted by the liquid 612 in the first portion 603-1 of the interior cavity 603. In some embodiments, a volume of the first portion 603-1 is greater than a volume encompassed by the manipulable portion 502 when the manipulable portion is in the deployed or expanded configuration.

These repeated movements facilitate removal of trapped bubbles of air or other undesired fluid from the manipulable portion 502. It is noted that seal 608a is typically manipulated to not seal against the exterior surface of the first part 510e-2 of the distal end portion 510e of the elongate shaft member 500a to permit the repeated movements of the manipulable portion 502 in the vessel 602. That is, the repeated movements of the manipulable portion 502 in the vessel 602 may require unfettered movement of at least the elongate shaft member 500a which may, in some embodiments, be provided when seal 608a is not sealing against the exterior surface of the first part 510e-2 of the distal end portion 510e of the elongate shaft member 500a. In situations in which the liquid in the first portion 603-1 of the interior cavity 603 is in a pressurized state (e.g., pressurized to flush first lumen 510d or still pressurized after having flushed first lumen 510d), the liquid may be depressurized according to various methods similar or identical to those discussed above to avoid an undesired expulsion of the pressurized liquid to the surrounding environment when the seal 608a is manipulated to not seal against the exterior surface of the first part 510e-2 of the distal end portion 510e of the elongate shaft member 500a.

After the elongate shaft member 500a has been flushed and trapped bubbles have been removed from the manipulable portion 502, the manipulable portion 502 may be moved into its unexpanded or delivery configuration and retracted into a proximal region 528a of the loading assembly 528, which may then be sealed at the distal end of the proximal region 528a via cap 513. The proximal region 528a of the loading assembly 528 may be disconnected from the distal region 528b, thereby allowing the proximal region 528a of the loading assembly 528, with the manipulable portion 502 therein, to be transported for subsequent insertion into a body (for example, via a coupling with a proximal end of elongate shaft member 500b of catheter sheath 512).

While some of the embodiments disclosed above are suitable for cardiac mapping, the same or similar embodiments may be used for mapping other bodily organs, for example gastric mapping, bladder mapping, arterial mapping and mapping of any bodily lumen, bodily chamber or bodily cavity into which the devices of the present invention may be introduced.

While some of the embodiments disclosed above are suitable for cardiac ablation, the same or similar embodiments may be used for ablating other bodily organs or any bodily lumen, bodily chamber or bodily cavity into which the devices of the present invention may be introduced.

Subsets or combinations of various embodiments described above can provide further embodiments.

These and other changes may be made to the invention in light of the above-detailed description. In general, in the following claims, the terms used should not be construed to limit the invention to the specific embodiments disclosed in the specification and the claims, but should be construed to include other catheter systems including all medical treatment catheter systems and medical diagnostic catheter systems in accordance with the claims. Accordingly, the invention is not limited by the disclosure, but instead its scope is to be determined entirely by the following claims.

What is claimed is:

1. A method of flushing a catheter, the catheter comprising an elongate shaft member that includes a proximal end, a distal end, a length from the proximal end to the distal end, and at least a first lumen extending between the proximal end and the distal end, wherein the first lumen comprises a first end spaced proximally from a second end, the second end located at least proximate the distal end of the elongate shaft member, and wherein the distal end of the elongate shaft member is arranged to be deliverable ahead of the proximal end of the elongate shaft member through a bodily opening leading to a bodily cavity, the length of the elongate shaft member sufficient to position the proximal end outside a body comprising the bodily cavity during a state in which the distal end is positioned in the bodily cavity, the catheter comprising a manipulable portion physically coupled to a distal end portion of the elongate shaft member, and the method comprising:

providing a vessel with the manipulable portion and at least part of the distal end portion of the elongate shaft member including the distal end of the elongate shaft member in an interior cavity of the vessel, the manipulable portion and the at least part of the distal end portion of the elongate shaft member including the distal end of the elongate shaft member protruding into the interior cavity of the vessel via a first port provided by the vessel, and the manipulable portion selectively moveable between an unexpanded configuration in which the manipulable portion is sized for delivery through the first port and an expanded configuration in which the manipulable portion is sized too large for delivery through the first port;

providing a quantity of a liquid into at least a first portion of the interior cavity of the vessel, the second end of the first lumen in fluid communication with the liquid provided in the first portion of the interior cavity;

establishing a flow of at least some of the liquid in the first portion of the interior cavity through the first lumen from the second end of the first lumen toward the first end of the first lumen to facilitate flushing of a fluid other than the liquid from the first lumen;

repeatedly moving the manipulable portion, when the manipulable portion is in the expanded configuration in the first portion of the interior cavity to agitate the liquid in the first portion of the interior cavity and facilitate air bubble removal from the manipulable portion; and removing the manipulable portion, in the unexpanded configuration, and the at least part of the distal end portion of the elongate shaft member from the interior cavity of the vessel into a loading assembly for subsequent delivery through the bodily opening leading to the bodily cavity.

2. The method of claim 1, wherein the vessel comprises a size too large for delivery of the vessel through the bodily opening leading to the bodily cavity at least in a state in which the first portion of the interior cavity is void of the liquid.

3. The method of claim 1, wherein the liquid in at least the first portion of the interior cavity is pressurized.

4. The method of claim 1, comprising pressurizing the liquid in at least the first portion of the interior cavity after the liquid is provided in the first portion of the interior cavity.

5. The method of claim 1, comprising pressurizing the liquid in at least the first portion of the interior cavity to establish the flow of at least some of the liquid in the first portion of the interior cavity through the first lumen from the second end of the first lumen toward the first end of the first lumen to facilitate flushing of the fluid other than the liquid from the first lumen.

6. The method of claim 1, comprising providing a particular fluid into a second portion of the interior cavity to pressurize the liquid provided in the first portion of the interior cavity.

7. The method of claim 6, wherein the particular fluid is different than the liquid.

8. The method of claim 6, wherein the providing the particular fluid into the second portion of the interior cavity to pressurize the liquid in the first portion of the interior cavity comprises providing the particular fluid into the second portion of the interior cavity via a second port provided by the vessel, and the method comprises removing at least some of the particular fluid from the second portion of the interior cavity to depressurize the liquid in the first portion of the interior cavity, the at least some of the particular fluid removed from the second portion of the interior cavity via a third port provided by the vessel, each of the second port and the third port being other than the first port.

9. The method of claim 8, wherein the third port is provided by the second port.

10. The method of claim 1, comprising providing a quantity of a particular fluid other than the liquid into a second portion of the interior cavity while at least some of the liquid is in the first portion of the interior cavity.

11. The method of claim 10, wherein the vessel comprises a second port in fluid communication with the interior cavity, the second port other than the first port, and wherein at least some of the quantity of the particular fluid is provided into the second portion of the interior cavity at least through the second port.

12. The method of claim 11, wherein the second port is arranged to prevent any reception of the distal end portion of the elongate shaft member when the distal end portion of the elongate shaft member is inserted into the interior cavity via the first port.

13. The method of claim 12, wherein the second port is positionable to permit a flow of the particular fluid through the second port while concurrently preventing a flow of the liquid through the second port.

14. The method of claim 11, wherein the vessel comprises a wall portion, and the method comprises moving at least part of the wall portion to exert pressure on the liquid in the first portion of the interior cavity, the pressure sufficient to cause the establishing the flow of the at least some of the liquid in the first portion of the interior cavity through the first lumen from the second end of the first lumen toward the first end of the first lumen to facilitate flushing of the fluid other than the liquid from the first lumen.

15. The method of claim 14, wherein the wall portion is provided between the first portion of the interior cavity and the second portion of the interior cavity.

16. The method of claim 11, wherein the vessel comprises a removable cap, the cap removable to provide access to the interior cavity and wherein both the first port and the second port are provided in the cap.

17. The method of claim 10, wherein the vessel comprises a conduit member comprising a first conduit end, a second conduit end, and a second lumen extending between the first conduit end and the second conduit end, and the method comprises conveying a flow of the particular fluid though the second lumen toward the second conduit end, wherein the second conduit end is arranged to provide at least some of the quantity of the particular fluid into the second portion of the interior cavity.

18. The method of claim 17, wherein the conduit member is arranged to locate the second conduit end at a location in the interior cavity away from the liquid provided in the first portion of the interior cavity.

19. The method of claim 18, wherein at least part of the conduit member extends across at least part of the first portion of the interior cavity.

20. The method of claim 17, wherein the conduit member is arranged to locate the second conduit end in the second portion of the interior cavity.

21. The method of claim 17, wherein the second lumen is arranged to prevent any reception of the distal end portion of the elongate shaft member when the distal end portion of the elongate shaft member is inserted into the interior cavity via the first port.

22. The method of claim 10, wherein the quantity of the particular fluid is sufficient to exert pressure on the liquid, and the pressure sufficient to cause the establishing the flow of the at least some of the liquid in the first portion of the interior cavity through the first lumen from the second end of the first lumen toward the first end of the first lumen to facilitate flushing of the fluid other than the liquid from the first lumen.

23. The method of claim 1, comprising providing a quantity of a particular fluid other than the liquid into a second portion of the interior cavity, wherein the quantity of the particular fluid is sufficient to exert pressure on the liquid in the first portion of the interior cavity, the pressure sufficient to cause the establishing the flow of the at least some of the liquid in the first portion of the interior cavity through the first lumen from the second end of the first lumen toward the first end of the first lumen to facilitate flushing of the fluid other than the liquid from the first lumen.

24. The method of claim 23, comprising providing the quantity of the particular fluid other than the liquid into the second portion of the interior cavity after the quantity of the liquid has been provided into at least the first portion of the interior cavity.

25. The method of claim 1, comprising providing a quantity of a particular fluid other than the liquid into a second portion of the interior cavity after the quantity of the liquid has been provided into at least the first portion of the interior cavity.

26. The method of claim 1, wherein the vessel comprises a removable cap, the cap removable to provide access to the interior cavity and wherein the first port is provided in the cap.

27. The method of claim 1, comprising manipulating a seal member to seal an exterior surface of the distal end portion of the elongate shaft member to at least part of the vessel, and subsequently, manipulating the seal member to unseal the exterior surface of the distal end portion of the elongate shaft member from the at least part of the vessel at least prior to a delivery of at least the distal end portion of the elongate shaft member through the bodily opening leading to the bodily cavity.

28. The method of claim 27, comprising pressurizing the liquid in the first portion of the interior cavity after the manipulating the seal member to seal the exterior surface of the distal end portion of the elongate shaft member to the at least part of the vessel but before the manipulating the seal member to unseal the exterior surface of the distal end portion of the elongate shaft member from the at least part of the vessel.

29. The method of claim 1, comprising moving the manipulable portion from the unexpanded configuration to the expanded configuration in the first portion of the interior cavity.

30. The method of claim 1, comprising moving the manipulable portion from the unexpanded configuration to the expanded configuration while the manipulable portion is wetted by the liquid provided in the first portion of the interior cavity.

31. The method of claim 1, comprising pressurizing the liquid in at least the first portion of the interior cavity after the liquid is provided in the first portion of the interior cavity to prevent fluid flow from the first lumen into the interior cavity.

* * * * *